(12) United States Patent
Xu et al.

(10) Patent No.: US 8,859,274 B2
(45) Date of Patent: Oct. 14, 2014

(54) ANTIBODY FRAGMENT-TARGETED IMMUNOLIPOSOMES FOR SYSTEMIC GENE DELIVERY

(75) Inventors: Liang Xu, Arlington, VA (US); Cheng-Cheng Huang, Arlington, VA (US); William Alexander, Rockville, MD (US); WenHua Tang, Arlington, VA (US); Esther H. Chang, Chevy Chase, MD (US)

(73) Assignees: SynerGene Therapeutics, Inc., Washington, DC (US); Georgetown University, Washington, DC (US)

( * ) Notice: Subject to any disclaimer, the term of this patent is extended or adjusted under 35 U.S.C. 154(b) by 570 days.

(21) Appl. No.: 11/591,478

(22) Filed: Nov. 2, 2006

(65) Prior Publication Data

US 2007/0065432 A1 Mar. 22, 2007

Related U.S. Application Data

(63) Continuation of application No. 09/914,046, filed as application No. PCT/US00/04392 on Feb. 22, 2000, now Pat. No. 7,479,276.

(60) Provisional application No. 60/121,133, filed on Feb. 22, 1999.

(51) Int. Cl.
| | |
|---|---|
| C12N 15/00 | (2006.01) |
| A01N 63/00 | (2006.01) |
| A61K 48/00 | (2006.01) |
| C12N 15/86 | (2006.01) |
| A61K 47/48 | (2006.01) |
| A61K 9/00 | (2006.01) |
| A61K 9/127 | (2006.01) |

(52) U.S. Cl.
CPC ............. *C12N 15/86* (2013.01); *A61K 48/0008* (2013.01); *C12N 2810/859* (2013.01); *A61K 47/48561* (2013.01); *A61K 9/0019* (2013.01); *C12N 2710/10343* (2013.01); *C12N 2810/85* (2013.01); *A61K 9/1271* (2013.01); *A61K 47/48823* (2013.01); *A61K 9/1272* (2013.01)
USPC ...................................... 435/320.1; 424/93.1

(58) Field of Classification Search
CPC .............. A61K 2300/00; A61K 38/00; A61K 2039/505; C12N 15/85; C07K 16/30
USPC ........................................ 435/320.1; 424/93.1
See application file for complete search history.

(56) References Cited

U.S. PATENT DOCUMENTS

| | | |
|---|---|---|
| 4,946,778 A | 8/1990 | Lander et al. |
| 5,624,820 A | 4/1997 | Cooper |
| 5,635,380 A | 6/1997 | Naftilan et al. |
| 5,674,703 A | 10/1997 | Woo et al. |
| 5,688,488 A | 11/1997 | Low et al. |
| 5,707,830 A | 1/1998 | Calos |
| 5,783,566 A | 7/1998 | Mislick |
| 5,786,214 A | 7/1998 | Holmberg |
| 5,851,818 A | 12/1998 | Huang et al. |
| 5,856,152 A * | 1/1999 | Wilson et al. ................. 435/457 |
| 5,977,322 A | 11/1999 | Marks et al. |
| 6,028,066 A | 2/2000 | Unger |
| 6,030,956 A | 2/2000 | Boulikas |
| 6,069,134 A | 5/2000 | Roth et al. |
| 6,071,533 A | 6/2000 | Papahadjopoulos et al. |
| 6,077,834 A | 6/2000 | Cheng |
| 6,099,842 A | 8/2000 | Pastan et al. |
| 6,200,956 B1 | 3/2001 | Scherman et al. |
| 6,210,707 B1 | 4/2001 | Papahadjopoulos et al. |
| 6,248,721 B1 | 6/2001 | Chang |
| 6,303,378 B1 | 10/2001 | Bridenbaugh et al. |
| 6,414,139 B1 | 7/2002 | Unger et al. |
| 6,448,390 B1 | 9/2002 | Albritton et al. |

(Continued)

FOREIGN PATENT DOCUMENTS

| | | |
|---|---|---|
| EP | 0 451 972 A2 | 10/1991 |
| JP | 09-110722 | 4/1997 |

(Continued)

OTHER PUBLICATIONS

Miralles et al., The adenovirus inverted terminal repeat functions as an enhancer in a cell-free system. J Biol Chem. 264(18):10763-72, 1989.*

(Continued)

*Primary Examiner* — Anoop Singh
*Assistant Examiner* — David A Montanari
(74) *Attorney, Agent, or Firm* — Fanelli Haag & Kilger PLLC

(57) ABSTRACT

A targeted vector allowing enhanced gene transfer to human hepato-cellular carcinoma (HCC[1]) cells in vitro was developed using cationic liposomes covalently conjugated with the mAb AF-20. This high affinity antibody recognizes a rapidly internalized 180 kDa cell surface glycoprotein which is abundantly expressed on the surface of human HCC and other cancer cells. Quantitative binding analysis of liposomes with target cells by flow cytometry showed specific association of mAb-targeted liposomes with human HCC cells. Using mAb-targeted cationic liposomes containing 20% DOTAP, in the presence or absence of serum, gene expression in HuH-7 cells was enhanced up to 40-fold as compared to liposomes conjugated with an isotype-matched non-relevant control antibody. Transfection specificity was not observed in a control cell line that does not express the antigen recognized by mAb AF-20. This study demonstrates that cationic liposome formulations can be targeted with monoclonal antibodies (mAbs) to enhance specific in vitro gene delivery and expression in the presence or absence of serum.

6 Claims, 9 Drawing Sheets

(56) References Cited

U.S. PATENT DOCUMENTS

| | | |
|---|---|---|
| 6,794,128 B2 | 9/2004 | Marks et al. |
| 2001/0008759 A1 | 7/2001 | Marks et al. |
| 2004/0209366 A1 | 10/2004 | Papahadjopoulos et al. |

FOREIGN PATENT DOCUMENTS

| | | | |
|---|---|---|---|
| WO | WO 83/02069 A1 | | 6/1983 |
| WO | WO 95/14380 A1 | | 6/1995 |
| WO | WO 95/21259 A1 | | 8/1995 |
| WO | WO 95/35301 A1 | | 12/1995 |
| WO | WO 97/10007 A1 | | 3/1997 |
| WO | WO 97/28817 A1 | | 8/1997 |
| WO | WO 98/20857 A1 | | 5/1998 |
| WO | PCT/DE98/01940 | * | 1/1999 |
| WO | WO 99/25320 A1 | | 5/1999 |
| WO | WO 99/59643 A2 | | 11/1999 |
| WO | WO 00/15649 A1 | | 3/2000 |

OTHER PUBLICATIONS

Gatto et al., The M4M5 cytoplasmic loop of the Na,K-ATPase, overexpressed in *Escherichia coli*, binds nucleoside triphosphates with the same selectivity as the intact native protein. J Biol Chem. 273(17):10578-85, 1998.*
Pignatelli et al., Genetic polymorphisms among human cytomegalovirus (HCMV) wild-type strains, Rev. Med. Virol. 14(6):383-410, 2004.*
Schmid et al., (1997, J. Virology, vol. 71(5), pp. 3375-3384).*
He et al. (1998, PNAS, vol. 95, pp. 2509-2514).*
Laukkanen et al. (1994, Biochemistry, vol. 33, pp. 11664-11670).*
Allen, T.M., et al., "A new strategy for attachment of antibodies to sterically stabilized liposomes resulting in efficient targeting to cancer cells," *Biochim. Biophys. Acta* 1237:99-108, Elsevier Science Inc. (1995).
Allen, T.M., et al., "Antibody-Targeted Stealth® Liposomes" in *Stealth Liposomes*, Lasic, D.D. and Martin, F.J., eds., CRC Press Inc., Boca Raton, FL, pp. 233-244 (1995).
Allen, T.M., "Liposomes. Opportunities in Drug Delivery," *Drugs* 54:8-14, Adis International Limited (1997).
Anderson, W.F., "Human gene therapy," *Nature* 392:25-30, Nature Publishing Group (Apr. 1998).
Aoki, K., et al., "Liposome-mediated in Vivo Gene Transfer of Antisense K-ras Construct Inhibits Pancreatic Tumor Dissemination in the Murine Peritoneal Cavity," *Cancer Res.* 55:3810-3816, American Association for Cancer Research (1995).
Bajoria, R., et al., "Endocytotic uptake of small unilamellar liposomes by human trophoblast cells in culture," *Hum. Reprod.* 12:1343-1348, European Society for Human Reproduction and Embryology (1997).
Bajoria, R., and Contractor, S.F., "Effect of Surface Charge of Small Unilamellar Liposomes on Uptake and Transfer of Carboxyfluorescein across the Perfused Human Term Placenta," *Pediatr. Res.* 42:520-527, International Pediatrics Research Foundation, Inc. (1997).
Bristow, R.G., et al., "The p53 gene as a modifier of intrinsic radiosensitivity: implications for radiotherapy," *Radiother. Oncol.* 40:197-223, Elsevier Scientific Publishers (1996).
Campbell, M.J., "Lipofection Reagents Prepared by a Simple Ethanol Injection Technique," *BioTechniques* 18:1027-1032, Eaton Publishing Co. (1995).
Chackal-Roy, M., et al., "Stimulation of Human Prostatic Carcinoma Cell Growth by Factors Present in Human Bone Marrow," *J. Clin. Invest.* 84:43-50, The American Society for Clinical Investigation, Inc. (1989).
Chen, L., et al., "Synergistic activation of p53 by inhibition of MDM2 expression and DNA damage," *Proc. Natl. Acad. Sci. USA* 95:195-200, National Academy of Sciences (1998).
Cheng, P.-W., "Receptor Ligand-Facilitated Gene Transfer: Enhancement of Liposome-Mediated Gene Transfer and Expression by Transferrin," *Hum. Gene Ther.* 7:275-282, Mary Ann Liebert, Inc. (1996).

Chiarugi, V., et al., "Cox-2, iNOS and p53 as play-makers of tumor angiogenesis (Review)," *Int. J. Mol. Med.* 2:715-719, D.A. Spandidos (1998).
Clark, P.R., and Hersh, E.M., "Cationic lipid-mediated gene transfer: Current concepts," *Curr. Opin. Mol. Ther.* 1:158-176, Current Drugs Ltd. (Apr. 1999).
Compagnon, B., et al., "Enhanced Gene Delivery and Expression in Human Hepatocellular Carcinoma Cells by Cationic Immunoliposomes," *J. Liposomes Res.* 7:127-141, Marcle Dekker, Inc. (1997).
Cristiano, R.J., and Curiel, D.T., "Strategies to accomplish gene delivery via the receptor-mediated endocytosis pathway," *Cancer Gene Ther.* 3:49-57, Appleton & Lange (1996).
Davidson, B.L., et al., "Expression of *Escherichia coli* β-Galactosidase and Rat HPRT in the CNS of *Macaca mulatta* Following Adenoviral Mediated Gene Transfer," *Experimental Neurology* 125:258-267, Academic Press, Inc. (1994).
de Kurif, J., et al., "Biosynthetically lipid-modified human scFv fragments from phage display libraries as targeting molecules for immunoliposomes," *FEBS Lett.* 399:232-236, Elsevier Science B.V. (1996).
Drummond, D.C., et al., "Optimizing Liposomes for Delivery of Chemotherapeutic Agents to Solid Tumors," *Pharmacol. Rev.* 51:691-743, The American Society for Pharmacology and Experimental Therapeutics (Dec. 1999).
Dubé, D., et al., "Preparation and Tumor Cell Uptake of Poly(N-isopropylacrylamide) Folate Conjugates," *Bioconjugate Chem.* 13:685-692, American Chemical Society (May-Jun. 2002).
Dzau, V.J., et al., "Fusigenic viral liposome for gene therapy in cardiovascular diseases," *Proc. Natl. Acad. Sci. USA* 93:11421-11425, National Academy of Sciences (1996).
Elliott, R.L., et al., "Breast Carcinoma and the Role of Iron Metabolism: A Cytochemical, Tissue Culture, and Ultrastructural Study," *Ann. N.Y. Acad. Sci.* 698:159-166, New York Academy of Sciences (1993).
Ellman, G.L., "Tissue Sulfhydryl Groups," *Arch. Biochem. Biophys.* 82:70-77, Academic Press (1959).
Feero, W.G., et al., "Selection and use of ligands for receptor-mediated gene delivery to myogenic cells," *Gene Therapy* 4:664-674, Nature Publishing Group (1997).
Felgner, P.L., et al., "Improved Cationic Lipid Formulations for In Vivo Gene Therapy," *Ann. N.Y. Acad. Sci.* 772:126-139, New York Academy of Sciences (1995).
Filion, M.C. and Phillips, N.C., "Toxicity and immunomodulatory activity of liposomal vectors formulated with cationic lipids toward immune effector cells," *Biochimica et Biophysica Acta* 1329:345-356, Elsevier Science Ltd. (1997).
Filion, M.C. and Phillips, N.C., "Major limitations in the use of cationic liposomes for DNA delivery," *International Journal of Pharmaceutics* 162:159-170, Elsevier Science Ltd. (1998).
Forssen, E., and Willis, M., "Ligand-targeted liposomes," *Adv. Drug Deliv. Rev.* 29:249-271, Elsevier Science B.V. (1998).
Fujiwara, T., et al., "A Retroviral Wild-Type p53 Expression Vector Penetrates Human Lung Cancer Spheroids and Inhibits Growth by Inducing Apoptosis," *Cancer Res.* 53:4129-4133, American Association for Cancer Research (1993).
Fujiwara, T., et al., "Induction of Chemosensitivity in Human Lung Cancer Cells in vivo by Adenovirus-mediated Transfer of the Wild-Type p53 Gene," *Cancer Res.* 54:2287-2291, American Association for Cancer Research (1994).
Gao, X. and Huang, L., "Potentiation of Cationic Liposome-Mediated Gene Delivery by Polycations," *Biochemistry* 35:1027-1036, American Chemical Society (1996)
Gershon, H., et al., "Mode of formation and structural features of DNA-cationic liposome complexes used for transfection," *Biochem.* 32:7143-7151, American Chemical Society (1993).
Grayhack, J.T., et al., "Analysis of Specific Proteins in Prostatic Fluid for Detecting Prostatic Malignancy," *J. Urol.* 121:295-299, The Williams & Wilkins Co. (1979)
Grimaldi, S., et al., "Attempts to use liposomes and RBC ghosts as vectors in drug and antisense therapy of virus infection," *Res. Virol.* 148:177-180, Elsevier Science Ltd. (1997).

(56) References Cited

OTHER PUBLICATIONS

Hamada, K., et al., "Adenovirus-mediated Transfer of a Wild-Type p53 Gene and Induction of Apoptosis in Cervical Cancer," *Cancer Res.* 56:3047-3054, American Association for Cancer Research (1996).
Hamada, K. et al., "Growth Inhibition of Human Cervical Cancer Cells with the Recombinant Adenovirus p53 in Vitro," *Gynecologic Oncology* 60:373-379, Academic Press, Inc. (1996)
Hamada, K., et al., "Adenovirus-Mediated Transfer of HPV 16 E6/E7 Antisense RNA to Human Cervical Cancer Cells," *Gynecologic Oncology* 63:219-227, Academic Press, Inc. (1996).
Haynes, B.F., et al., "Characterization of a Monoclonal Antibody (5E9) That Defines a Human Cell Surface Antigen of Cell Activation," *J. Immunol.* 127:347-351, American Association of Immunologists (1981).
He, Y. and Huang, L., "Growth Inhibition of Human Papillomavirus 16 DNA-positive Mouse Tumor by Antisense RNA Transcribed from U6 Promoter," *Cancer Research* 57:3993-3999, American Association for Cancer Research (1997).
Huwyler, J., et al., "Brain drug delivery of small molecules using immunoliposomes," *Proc. Natl. Acad. Sci. USA* 93:14164-14169, National Academy of Sciences (1996).
Jiang, A., et al., "Cell-Type-Specific Gene Transfer into Human Cells with Retroviral Vectors that Display Single-Chain Antibodies," *J. Virol.* 72:10148-10156, American Society for Microbiology (Dec. 1998).
Johnson, P., et al., "Expression of Wild-Type p53 Is Not Compatible with Continued Growth of p53-Negative Tumor Cells," *Mol. Cell Biol.* 11:1-11, American Society for Microbiology (1991).
Kao, G.Y., et al., "Use of targeted cationic liposomes in enhanced DNA delivery to cancer cells," *Cancer Gene Therapy* 3:250-256, Nature Publishing Group (1996).
Keer, H.N., et al., "Elevated Transferrin Receptor Content in Human Prostate Cancer Cell Lines Assessed In Vitro and In Vivo," *J. Urol.* 143:381-385, American Urological Association, Inc. (1990).
Kerr, J.F.R., et al., "Apoptosis: Its Significance in Cancer and Cancer Therapy," *Cancer* 73:2013-2026, Wiley (1994).
Kirpotin, D., et al.,"Sterically Stabilized Anti-HER2 Immunoliposomes: Design and Targeting to Human Breast Cancer Cells in Vitro," *Biochemistry* 36:66-75, American Chemical Society (1997).
Kobatake, E., et al., "A fluoroimmunoassay based on immunoliposomes containing genetically engineered lipid-tagged antibody," *Anal. Chem.* 69:1295-1298, American Chemical Society (1997).
Koning, G.A., et al., "Antiproliferative effect of immunoliposomes containing 5-fluorodeoxyuridine-dipalmitate on colon cancer cells," *Br. J. Cancer* 80:1718-1725, Cancer Research Campaign (Aug. 1999).
Koning, G.A., et al., "Selective transfer of a lipophilic prodrug of 5-fluorodeoxyuridine from immunoliposomes to colon cancer cells," *Biochim. Biophys. Acta* 1420:153-167, Elsevier Science B.V. (Aug. 1999).
Konishi, H., et al., "Targeting Strategy for Gene Delivery to Carcinoembryonic Antigen-Producing Cancer Cells by Retrovirus Displaying a Single-Chain Variable Fragment Antibody," *Hum. Gene Ther.* 9:235-248, Mary Ann Liebert, Inc. (1998).
Lappalainen, K., et al., "Cationic liposomes mediated delivery of antisense oligonucleotides targeted to HPV 16 E7 mRNA in CaSki cells," *Antiviral Research* 23:119-130, Elsevier Science B.V. (1994).
Lasic, D.D., et al., "Sterically stabilized liposomes in cancer therapy and gene delivery," *Curr. Opin. Mol. Ther.* 1:177-185, Current Drugs Ltd. (Apr. 1999).
Lasic, D.D., and Papahadjopoulos, D., "Liposomes Revisited," *Science* 267:1275-1276, American Association for the Advancement of Science (1995).
Laukkanen, M.-L., et al., "Functional Immunoliposomes Harboring a Biosynthetically Lipid-Tagged Single-Chain Antibody," *Biochemistry* 33:11664-11670, American Chemical Society (1994).

Lavigne, C. and Thierry, A.R., "Enhanced Antisense Inhibition of Human Immunodeficiency Virus Type 1 in Cell Cultures by DLS Delivery System," *Biochemical and Biophysical Research Communications* 237:566-571, Academic Press (1997).
Ledley, F.D., "Nonviral Gene Therapy: The Promise of Genes as Pharmaceutical Products," *Hum. Gene Ther.* 6:1129-1144, Mary Ann Liebert, Inc. (1995).
Lee, R.J. and Huang, L., "Lipidic Vector Systems for Gene Transfer," *Critical Reviews in Therapeutic Drug Carrier Systems* 14:173-206, Begell House, Inc. (1997).
Lee, R.J and Low, P.S., "Delivery of Liposomes into Cultured KB Cells via Folate Receptor-mediated Endocytosis," *J. Biol. Chem.* 269:3198-3204, The American Society for Biochemistry and Molecular Biology, Inc. (1994).
Lee, R.J. and Huang, L., "Folate-targeted, Anionic Liposome-entrapped Polylysine-condensed DNA for Tumor Cell-specific Gene Transfer," *J. Biol. Chem.* 271:8481-8487, American Society for Biochemistry and Molecular Biology, Inc. (1996).
Lesoon-Wood, L.A., et. al., "Systemic gene therapy with p53 reduces growth and metastases of a malignant human breast cancer in nude mice," *Human Gene Therapy* 6:395-405, M.A. Liebert (1995).
Lewis, J.G., et al., "A serum-resistant cytofectin for cellular delivery of antisense oligodeoxynucleotides and plasmid DNA," *Proc. Natl. Acad. Sci. USA* 93:3176-3181, National Academy of Sciences (1996).
Li, S., and Huang, L., "Functional Pleomorphism of Liposomal Gene Delivery Vectors—Lipoplex and Lipopolyplex," in *Liposomes—Rational Design*, Janoff, A.S., ed., Marcel Dekker, Inc., New York, NY, pp. 89-124 (1998).
Liposome Technology, $2^{nd}$ Ed., vol. III, Table of Contents, Gregoriadis, G., ed., CRC Press, Boca Raton, Fla. (1992).
Liu, T.J., et al., "Growth Suppression of Human Head and Neck Cancer Cells By the Introduction of a Wild-Type p53 Gene via a Recombinant Adenovirus," *Cancer Res.* 54:3662-3667, American Association for Cancer Research (1994).
Lowe, S.W., "Cancer therapy and p53," *Curr. Opin. Oncol.* 7:547-553, Rapid Science Publishers (1995).
Maclean, A.L., et al., "Immunoliposomes as targeted delivery vehicles for cancer therapeutics," *Int. J. Oncol.* 11:325-332, D.A. Spandidos (1997).
Martin, F., et al., "Retroviral Vector Targeting to Melanoma Cells by Single-Chain Antibody Incorporation in Envelope," *Human Gene Ther.* 9:737-746, Mary Ann Liebert, Inc. (1998).
Martin, F.J. and Papahadjopoulos, D., "Irreversible Coupling of Immunoglobulin Fragments to Performed Vesicles an improved method for liposome targeting," *J. Biol. Chem.* 257:286-288, American Society for Biochemistry and Molecular Biology (1982).
Massing, U., "Cancer therapy with liposomal formulations of anticancer drugs," *Int. J. Clin. Pharmacol. Ther.* 35:87-90, Dustri-Verlag Dr. K. Feistle (1997).
Matlashewski, G., "p53: Twenty years on, Meeting Review," *Oncogene Rev.* 18:7618-7620, Stockton Press (Dec. 1999).
Miyamoto, T., et al., "Transferrin receptor in oral tumors," *Int. J. Oral Maxillofac. Surg.* 23:430-433, Munksgaard (1994).
Miyashita, T., et al., "Tumor suppressor p53 is a regulator of bcl-2 and bax gene expression in vitro and in vivo," *Oncogene* 9:1799-1805, Macmillan Press Ltd. (1994).
Morishige, H., et al., "In vitro cytoastic effect of TNF (Tumor Necrosis Factor) entrapped in immunoliposomes on cell normall to TNF," *Biochem. Biophys. Acta* 1151: 59-68, Elsevier Pub. Co (1993).
Morishita, R., et al., "Molecular Delivery System for Antisense Oligonucleotides: Enhanced Effectiveness of Antisense Oligonucleotides by HVJ-liposome Mediated Transfer," *J. Cardiovasc. Pharmacol. Therapeut.* 2:213-222, Westminster Publications (1996).
Nag, A., et al., "A Colorimetric Estimation of Polyethyleneglycol-Conjugated Phospholipid in Stealth Liposomes," *Anal. Biochem.* 250:35-43, Academic Press (1997).
Nam, S.M., et al., "Sterically Stabilized Anti-$G_{M3}$, anti-Le$^x$ Immunoliposomes: Targeting to B16BL6, HRT-18 Cancer Cells," *Oncol. Res.* 11:9-16, Cognizant Communication Corporation (Jul. 1999).

(56) References Cited

OTHER PUBLICATIONS

Ng, K.-Y., et al., "The effects of polyethyleneglycol (PEG)-derived lipid on the activity of target-sensitive immunoliposome," *Int. J. Pharma.* 193:157-166, Elsevier Science B.V. (Jan. 2000).

Nicholson, I.C., et al., "Construction and Characterisation of a Functional CD19 Specific Single Chain Fv Fragment for Immunotherapy of B Lineage Leukaemia and Lymphoma," *Mol. Immunol.* 34:1157-1165, Elsevier Science Ltd. (1997).

Nilsson, B., et. al., "Fusion protein in biotechnology and structural biology," *Curr. Opin. Struct. Biol.* 2:569-575, Current Biology (1992).

Nishikawa, M. and Huang, L., "Nonviral Vectors in the New Millenium: Delivery Barriers in Gene Transfer," *Human Gene Therapy* 12:861-870, Mary Ann Liebert, Inc. (May 2001).

Pagnan, G., et al., "GD2-Mediated Melanoma Cell Targeting and Cytotoxicity of Liposome-Entrapped Fenretinide," *Int. J. Cancer* 81:268-274, Wiley-Liss, Inc. (Apr. 1999).

Park, J.W., et al., "Immunoliposomes for cancer treatment," *Adv. Pharmacol*, 40:399-435, Academic Press (1997).

Park, J.W., et al., "Tumor targeting using anti-her2 immunoliposomes," *J. Control. Rel.* 74:95-113, Elsevier Science B.V. (Jul. 2001).

Park, J.W., et al., "Development of anti-p185$^{HER2}$ immunoliposomes for cancer therapy," *Proc. Natl. Acad. Sci. USA* 92:1327-1331, National Academy of Sciences (1995).

Pirollo, K.F., et al., "p53 mediated sensitization of squamous cell carcinoma of the head and neck to radiotherapy," *Oncogene* 14:1735-1746, Stockton Press (1997).

Pirollo, K.F., et al., "Immunoliposomes: A Targeted Delivery Tool for Cancer Treatment," in *Vector Targeting for Therapeutic Gene Delivery*, Curiel, D.T., and Douglas, J.T., eds., Wiley-Liss, Inc., Hoboken, NJ, pp. 33-62 (Aug. 2002).

Plank, C., et al., "Activation of the Complement System by Synthetic DNA Complexes: A Potential Barrier for Intravenous Gene Delivery," *Human Gene Therapy* 7:1437-1446, Mary Ann Liebert, Inc. (1996).

Poon, R.Y.M, "Advances in Monoclonal Antibody Applications: Bispecific Antibodies" in *Biotechnology International: International Developments in the Biotechnology Industry*, Fox, F., and Connor, T.H., eds., Universal Medical Press, Inc., San Francisco, CA, pp. 113-128 (1997).

Rait, A.S., et al., "Inhibitory effects of the combination of HER-2 antisense oligonucleotide and chemotherapeutic agents used for the treatment of human breast cancer," *Cancer Gene Ther.* 8:728-739, Nature Publishing Group (Oct. 2001).

Rait, A.S., et al., "Tumor-targeting, Systemically Delivered Antisense HER-2 Chemosensitizes Human Breast Cancer Xenografts Irrespective of HER-2 Levels," *Molecular Medicine* 8:475-486, North Shore LIJ Research Institute (2002).

Renneisen, K., et al., "Inhibition of Expression of Human Immunodeficiency Virus-1 in Vitro by Antibody-targeted Liposomes Containing Antisense RNA to the env Region," *J. Biol. Chem.* 265:16337-16342, American Society for Biochemistry and Molecular Biology (1990).

Riddles, P.W., et al., "Reassessment of Ellman's Reagent," *Methods Enzymol.* 91:49-60, Academic Press (1993).

Roh, H., et al., "HER2/neu antisense targeting of human breast carcinoma," *Oncogene* 19:6138-6143, Macmillan Publishers Ltd. (Dec. 2000).

Ropert, C., et al., "Oligonucleotides Encapsulated in pH Sensitive Liposomes are Efficient Toward Friend Retrovirus," *Biochemical and Biophysical Research Communications* 183:879-885, Academic Press (1992).

Rossi, M.C. and Zetter, B.R., "Selective stimulation of prostatic carcinoma cell proliferation by transferrin," *PNAS* 89:6197-6201, National Academy of Sciences (1992).

Ruley, H.E., "p53 and Response to Chemotherapy and Radiotherapy," in *Important Adv. Oncol.* 1996, DeVita, V.T., et al., eds., Lippincott-Raven Publishers, Philadelphia, PA, pp. 37-56 (1996).

Schier, R., et al., "In vitro and in vivo characterization of a human anti-c-erbB-2 single-chain Fv isolated from a filamentous phage antibody library," *Immunotechnology* 1:73-81, Elsevier Science B.V. (1995).

Seth, P., et al., "Adenovirus-mediated Gene Transfer to Human Breast Tumor Cells: An Approach for Cancer Gene Therapy and Bone Marrow Purging," *Cancer Res.* 56:1346-1351, American Association for Cancer Research (1996).

Seung, L.P., et al., "Genetic Radiotherapy Overcomes Tumor Resistance to Cytotoxic Agents," Cancer Res. 55:5561-5565, American Association for Cancer Research (1995).

Shahinian, S., and Silivius, J.R., "A novel strategy affords high-yield coupling of antibody Fab' fragments to liposomes," *Biochim. Biophys. Acta* 1239:157-167, Elsevier Science B.V. (1995).

Sidransky, D., and Hollstein, M., "Clinical implications of the p53 gene," *Annu. Rev. Med.* 47:285-301, Annual Reviews, Inc. (1996).

Simões, S., et al., "Enhancement of Cationic Liposome-Mediated Gene Delivery by Transferrin and Fusogenic Peptides," *Proceedings of the 24th International Symposium on Controlled Release of Bioactive Materials* 24:659-660, Jun. 15-19, 1997.

Shen, D.-F., et al., "An Improved Method for Covalent Attachment of Antibody to Liposomes," *Biochim. Biophys. Acta* 689:31-37, Elsevier Biomedical Press (1982).

Spragg, D.D., et al., "Immunotargeting of liposomes to activated vascular endothelial cells: A strategy for site-selective delivery in the cardiovascular system," *Proc. Natl. Acad. Sci. USA* 94:8795-8800, National Academy of Sciences (1997).

Srivastava, S., et al., "Recombinant Adenovirus Vector Expressing Wild-type p53 is a Potent Inhibitor of Prostate Cancer Cell Proliferation," *Urology* 46:843-848, Excerpta Medica, Inc. (1995).

Suzuki, S., et al., "Modulation of doxorubicin resistance in a doxorubicin-resistant human leukaemia cell by an immunoliposome targeting transferring receptor," *Br. J. Cancer* 76:83-89, Cancer Research Campaign (1997).

The Journal of Gene Medicine Clinical Trials Database, "Gene Therapy Clinical Trials Worldwide," available online at http://www.wiley.co.uk/wileychi/genmed/clinical, John Wiley and Sons, Ltd., 2 pages (accessed Sep. 2001).

Thierry, A.R., et al., "Systemic gene therapy: Biodistribution and long-term expression of a transgene in mice," *Proc. Natl. Acad. Sci. USA* 92:9742-9746, National Academy of Science (1995).

Thorstensen, K. and Romslo, I., "The Transferrin Receptor: Its Diagnostic Value and its Potential as Therapeutic Target," *Scand. J. Clin. Lab. Invest.* 53 (Suppl. 215):113-120, Universitetsforlaget (1993).

Verma, I.M. and Somia, N., "Gene therapy-promises, problems and prospects," *Nature* 389:239-242, Nature Publishing Group (1997).

Vertut-Doï, A., et al., "Binding and uptake of liposomes containing a poly(ethylene glycol) derivative of cholesterol (stealth liposomes) by the macrophage cell line J774: influence of PEG content and its molecular weight," *Biochim. Biophys. Acta* 1278:19-28, Elsevier Science B.V. (1996)

Volpert, O.V., et al., "Sequential development of an angiogenic phenotype by human fibroblasts progressing to tumorigenicity," *Oncogene* 14:1495-1502, Stockton Press (1997)

Wagner, E., et al., "Influenza virus hemagglutinin HA-2 N-terminal fusogenic peptides augment gene transfer by transferrin-polylysine-DNA complexes: Toward a synthetic virus-like gene-transfer vehicle," *Proc. Natl. Acad. Sci. USA* 89:7934-7938, National Academy of Sciences (1992).

Wang, S., et al., "Delivery of antisense oligodeoxyribonucleotides against the human epidermal growth factor receptor into cultured KB cells with liposomes conjugated to folate via polyethylene glycol," *PNAS* 92:3318-3322, National Academy of Science (1995).

Wang, D., et al., "Generation and Characterization of an Anti-CD19 Single-Chain Fv Immunotoxin Composed of C-Terminal Disulfide-Linked dgRTA," *Bioconjug. Chem* 8:878-884, American Chemical Society (1997).

Weinberg, E.D., "Roles of Iron in Neoplasia: Promotion, Prevention, and Therapy," *Biol. Trace Element Res.* 34:123-140, Humana Press, Inc. (1992).

(56) References Cited

OTHER PUBLICATIONS

Wright, S.E. and Huang, L., "Bilayer stabilization of phosphatidylethanolamine by N-biotinylphosphatidylethanolamine," *Biochim. Biophys. Acta* 1103:172-178, Elsevier Pub. Co (1992).

Xu, M., et al., "Parenteral Gene Therapy with p53 Inhibits Human Breast Tumors In Vivo Through a Bystander Mechanism Without Evidence of Toxicity," *Human Gene Therapy* 8:177-185, Mary Ann Liebert, Inc. (1997).

Xu, L., et al., "Transferrin-Liposome-Mediated p53 Sensitization of Squamous Cell Carcinoma of the Head and Neck to Radiation In Vitro," *Human Gene Therapy* 8:467-475, M.A. Liebert (1997).

Xu, L., et al., "Transferrin-Liposome-Mediated Systemic p53 Gene Therapy in Combination with Radiation Results in Regression of Human Head and Neck Cancer Xenografts," *Hum. Gene Ther.* 10:2941-2952, Mary Ann Liebert, Inc. (Dec. 1999).

Xu, L., et al., "Self-Assembly of a Virus-Mimicking Nanostructure System for Efficient Tumor-Targeted Gene Delivery," *Hum. Gene Ther.* 13:469-481, Mary Ann Liebert, Inc. (Feb. 2002).

Xu, L., et al., "Systemic Tumor-targeted Gene Delivery by Anti-Transferin Receptor scFv-Immunoliposomes," *Mol. Cancer Ther.* 1:337-346, American Association for Cancer Research (Mar. 2002).

Xu, L., et al., "Systemic p53 Gene Therapy of Cancer with Immunolipoplexes Targeted by Anti-Transferrin Receptor scFv," *Molecular Medicine* 7:723-734, The Picower Institute Press (2001).

Xu, L., et al., "Systemic p53 gene therapy in combination with radiation results in human tumor regression," *Tumor Targeting* 4:92-104, Stockton Press (Jul. 1999).

Yang, C., et al., "Adenovirus-mediated Wild-Type p53 Expression Induces Apoptosis and Suppresses Tumorigenesis of Prostatic Tumor Cells," *Cancer Res.* 55:4210-4213, American Association for Cancer Research (1995).

Yazdi, P.T., et al., "Influence of Cellular Trafficking on Protein Synthesis Inhibition of Immunotoxins Directed against the Transferrin Receptor," *Cancer Res.* 55:3763-3771, American Association for Cancer Research (1995).

Yu, D., et al., "Liposome-mediated in vivo E1A gene transfer suppressed dissemination of ovarian cancer cells that overexpress HER-2/neu," *Oncogene* 11:1383-1388, Nature Publishing Group (1995).

Yoshida, J. and Mizuno, M., "Simple Preparation and Characterization of Cationic Liposomes Associated with a Monoclonal Antibody Against Glioma-Associated Antigen (Immunoliposomes)," *J. Liposome Res.* 5:981-995, Taylor & Francis (1995).

Zelphati, O., et al., "Synthesis and anti-HIV activity of thiocholesteryl-coupled phosphodiester antisense oligonucleotides incorporated into immunoliposomes," *Antiviral Research* 25:13-25, Elsevier Science Ltd. (1994)

Zelphati, O., et al., "Antisense oligonucleotides in solution or encapsulated in immunoliposomes inhibit replication of HIV-1 by several different mechanisms," *Nucleic Acids Research* 22:4307-4314, Oxford University Press (1994).

Zhang, W.-W., et al., "Advances in Cancer Gene Therapy," *Adv. Pharmacol.* 32:289-341, Academic Press, Inc. (1995).

Zhang, W.-W., et al., "High-efficiency gene transfer and high-level expression of wild-type p53 in human lung cancer cells mediated by recombinant adenovirus," *Cancer Gene Therapy* 1:5-13, Nature Publishing Group (1994).

Co-pending U.S. Appl. No. 09/914,046, inventors Xu, L., et al., filed Oct. 1, 2001 (Not Published).

Database Medline, Accession No. NLM7621238, English language abstract for Zhang, W.W., et al., "High-efficiency gene transfer and high-level expression of wild-type p53 in human lung cancer cells mediated by recombinant adenovirus," *Cancer Gene Therapy* 1:5-13, Nature Publishing Group (1994).

International Search Report for International Application No. PCT/US98/24657, mailed on Apr. 12, 1999, European Patent Office, Netherlands.

International Search Report for International Application No. PCT/US00/04392, mailed on Sep. 14, 2000, European Patent Office, The Netherlands.

Frank L. Graham, "Adenovirus Vectors for Gene Expression and Gene Therapy", *Transfus. Sci.* 17:15-27, 1996, Great Britain.

Davidson et al., Expression of *Escherichia coli* β-Galactosidase and Rat HPRT in the CNS of *Macaca mulatta* Following Adenoviral Mediated Gene Transfer, *Experimental Neurology* 125:258-267 (1994).

Danthinne, X., et al.: "Production of First Generation Adenovirus Vectors: A Review," *Gene Therapy*, vol. 7, p. 1707-1714, 2000.

Hearing, Patrick, et al.: "The Adenovirus Type 5 E1A Enhancer Contains Two Functionally Distinct Domains: One is Specific for E1A and the Other Modulates All Early Units in Cis," *Cell*, vol. 45, p. 229-236, 1986.

Logan, John S., et al.: "Transcriptional and Translational Control of Adenovirus Gene Expression," *Microbiological Reviews*, vol. 46, p. 377-383, 1982.

\* cited by examiner

ANTIBODY FRAGMENT-TARGETED IMMUNOLIPOSOMES FOR SYSTEMIC GENE DELIVERY

This application is a continuation application of currently pending U.S. application Ser. No. 09/914,046, filed Oct. 1, 2001, which is a national phase filing under 35 U.S.C. §371 of International Appl. No. PCT/US00/04392, filed Feb. 22, 2000, which claims priority to U.S. Provisional Application No. 60/121,133, filed Feb. 22, 1999.

BACKGROUND OF THE INVENTION

This invention provides methods for the preparation of antibody fragment-targeted liposomes ("immunoliposomes"), including lipid-tagged antibody fragment-targeted liposomes, methods for in vitro transfection using the immunoliposomes, and methods for systemic gene delivery in vivo. The liposomes of the present invention are useful for carrying out targeted gene delivery and efficient gene expression after systemic administration. The specificity of the delivery system is derived from the targeting antibody fragments.

An ideal therapeutic for cancer would be one that selectively targets a cellular pathway responsible for the tumor phenotype and which is nontoxic to normal cells. While cancer treatments involving gene therapy have substantial promise, there are many issues that need to be addressed before this promise can be realized. Perhaps foremost among the issues associated with macromolecular treatments is the efficient delivery of the therapeutic molecules to the site(s) in the body where they are needed. A variety of delivery systems (a.k.a. "vectors") have been tried including viruses and liposomes. The ideal delivery vehicle would be one that could be systemically (as opposed to locally) administered and which would thereafter selectively target tumor cells wherever they occur in the body.

The infectivity that makes viruses attractive as delivery vectors also poses their greatest drawback. Consequently, a significant amount of attention has been directed towards non-viral vectors for the delivery of molecular therapeutics. The liposome approach offers a number of advantages over viral methodologies for gene delivery. Most significantly, since liposomes are not infectious agents capable of self-replication, they pose no risk of transmission to other individuals. Targeting cancer cells via liposomes can be achieved by modifying the liposomes so that they selectively deliver their contents to tumor cells. There now exists a significant knowledge base regarding specific molecules that reside on the exterior surfaces of certain cancer cells. Such cell surface molecules can be used to target liposomes to tumor cells, because the molecules that reside upon the exterior of tumor cells differ from those on normal cells.

The publications and other materials used herein to illuminate die background of the invention or provide additional details respecting the practice, are incorporated by reference.

Current somatic gene therapy approaches employ either viral or non-viral vector systems. Many viral vectors allow high gene transfer efficiency but are deficient in certain areas (Ledley F D, et al. *Hum. Gene Ther.* (1995) 6:1129-1144). Non-viral gene transfer vectors circumvent some of the problems associated with using viral vectors. Progress has been made toward developing non-viral, pharmaceutical formulations of genes for in vivo human therapy, particularly cationic liposome-mediated gene transfer systems (Massing U, et al., *Int. J. Clin. Pharmacol. Ther.* (1997) 35:87-90). Features of cationic liposomes that make them versatile and attractive for DNA delivery include: simplicity of preparation; the ability to complex large amounts of DNA; versatility in use with any type and size of DNA or RNA; the ability to transfect many different types of cells, including non-dividing cells; and lack of immunogenicity or biohazardous activity (Felgner P L, et al., *Ann. NY Acad. Sci.* (1995) 772:126-139; Lewis J G, et al., *Proc. Natl. Acad Sci. USA* (1996) 93:3176-3181). More importantly from the perspective of human cancer therapy, cationic liposomes have been proven to be safe and efficient for in vivo gene delivery (Aoki K et al., *Cancer Res.* (1997) 55:3810-3816; Thierry A R, *Proc. Natl. Acad. Sci. USA* (1997) 92:9742-9746). More than thirty clinical trials are now underway using cationic liposomes for gene therapy (Zhang W et al., *Adv. Pharmacology* (1997) 32:289-333; RAC Committee Report: Human Gene Therapy Protocols—December 1998), and liposomes for delivery of small molecule therapeutics (e.g., antifungal and conventional chemotherapeutic agents) are already on the market (Allen T M, et al., *Drugs* (1997) 54 Suppl 4:8-14).

The transfection efficiency of cationic liposomes can be dramatically increased when they bear a ligand recognized by a cell surface receptor. Receptor-mediated endocytosis represents a highly efficient internalization pathway present in eukaryotic surface (Cristiano R J, et al., *Cancer Gene Ther.* (1996) 3:49-57, Cheng P W, *Hum. Gene Ther.* (1996) 7:275-282). The presence of a ligand on a liposome facilitates the entry of DNA into cells through initial binding of ligand by its receptor on the cell surface followed by internalization of the bound complex. A variety of ligands have been examined for their liposome-targeting ability, including transferrin and folate (Lee R J, et al., *J. Biol. Chem.* (1996) 271:8481-8487). Transferrin receptors (TfR) levels are elevated in various types of cancer cells including prostate cancers, even those prostate cell lines derived from human lymph node and bone metastases (Keer H N et al., *J. Urol.* (1990) 143:381-385); Chackal-Roy M et al., *J. Clin. Invest.* (1989) 84:43-50; Rossi M C, et al., *Proc. Natl. Acad. Sci. USA* (1992) 89:6197-6201; Grayhack J T. et al., *J. Urol.* (1979) 121:295-299). Elevated TfR levels also correlate with the aggressive or proliferative ability of tumor cells (Elliot R L, et al., *Ann. NY Acad Sci.* (1993) 698:159-166). Therefore, TfR levels are considered to be useful as a prognostic tumor marker, and TfR is a potential target for drug delivery in the therapy of malignant cells (Miyamoto T, et al., *Int. J. Oral Maxillofac. Surg.* (1994) 23:430-433:, Thorstensen K. et al., *Scand. J. Clin. Lab. Invest. Suppl.* (1993) 215:113-120). In our laboratory, we have prepared transferrin-complexed cationic liposomes with tumor cell transfection efficiencies in SCCHN of 60%-70%, as compared to only 5-20% by cationic liposomes without ligand (Xu L. et al., *Hum. Gene Ther.* (1997) 8:467-475).

In addition to the use of ligands that are recognized by receptors on tumor cells, specific antibodies can also be attached to the liposome surface (Allen T M et al., (1995) *Stealth Liposomes*, pp. 233-244) enabling them to be directed to specific tumor surface antigens (including but not limited to receptors) (Allen T M, *Biochim. Biophys. Acta* (1995) 1237:99-108). These "immunoliposomes," especially the sterically stabilized immunoliposomes, can deliver therapeutic drugs to a specific target cell population (Allen T M, et al., (1995) *Stealth Liposomes*, pp. 233-244). Park, et al. (Park J W, et al., *Proc. Natl. Acad Sci. USA* (1995) 92:1327-1331) found that anti-HER-2 monoclonal antibody (Mab) Fab fragments conjugated to liposomes could bind specifically to HER-2 overexpressing breast cancer cell line SK-BR-3. The immunoliposomes were found to be internalized efficiently by receptor-mediated endocytosis via the coated pit pathway and also possibly by membrane fusion. Moreover, the anchoring of anti-HER-2 Fab fragments enhanced their inhibitory effects. Doxorubicin-loaded anti-HER-2 immunoliposomes also showed significant and specific cytotoxicity against target cells in vitro and in vivo (Park J W, et al., *Proc. Natl. Acad. Sci. USA* (1995) 92:1327-1331). In addition, Suzuki et al., (Suzuki S, et al., *Br. J. Cancer* (1997) 76:83-89) used an anti-transferrin receptor monoclonal antibody conjugated immunoliposome to deliver doxorubicin more effectively in human leukemia cells in vitro. Huwyler et al. (Huwyler J, et al., *Proc. Natl. Acad. Sci. USA* (1996) 93:14164-14169) used anti-TfR monoclonal antibody immunoliposome to deliver daunomycin to rat glioma (RT2) cells in vivo. This PEGylated immunoliposome resulted in a lower concentration of the drug in normal tissues and organs. These studies demonstrated the utility of immunoliposomes for tumor-targeting drug delivery. It should be noted that the immunoliposome complexes used by Suzuki et al. and Huwyler et al. differ from those of the invention described herein in that they are anionic liposomes and that the methods used by Suzuki et al. and Huwyler et al. are not capable of delivering nucleic acids.

Single-chain Antibody Fragments

Progress in biotechnology has allowed the derivation of specific recognition domains from Mab (Poon R Y, (1997) *Biotechnology International: International Developments in the Biotechnology Industry*, pp. 113-128). The recombination of the variable regions of heavy and light chains and their integration into a single polypeptide provides the possibility of employing single-chain antibody derivatives (designated scFv) for targeting purposes. Retroviral vectors engineered to display scFv directed against carcinoembryonic antigen, HER-2, CD34, melanoma associated antigen and transferrin receptor have been developed (Jiang A, et al., *J. Virol*. (1998) 72:10148-10156, Konishi H, et al., *Hum. Gene Ther*. (1994) 9:235-248:, Martin F, et al., *Hum. Gene Ther*. (1998) 9:737-746). These scFv directed viruses have been shown to target, bind to and infect specifically the cell types expressing the particular antigen. Moreover, at least in the case of the carcinoembryonic antigen, scFv was shown to have the same cellular specificity as the parental antibody (Nicholson I C, *Mol. Immunol*. (1997) 34:1157-1165).

The combination of cationic liposome-gene transfer and immunoliposome techniques appears to be a promising system for targeted gene delivery.

SUMMARY OF THE INVENTION

We constructed a variety of immunoliposomes that are capable of tumor-targeted, systemic delivery of nucleic acids for use in human gene therapy. Based upon the data given in the Examples below these immunoliposome-DNA complexes incorporating the TfRscFv are capable of producing a much higher level of transfection efficiency than the same liposome-DNA complex bearing the complete Tf molecule. Therefore, in one aspect of the invention the immunoliposomes of the invention can be used to produce a kit for high efficiency transfection of various mammalian cell types that express the transferrin receptor. In one aspect of the invention, we constructed an scFv protein with a lipid tag such that the lipid is added naturally by the bacterial cell to allow easy incorporation of the scFv into liposomes while also avoiding chemical reactions which can inactivate the scFv.

The lipid-tagged scFv-immunoliposomes are prepared basically by two methods: a lipid-film solubilization method and a direct anchoring method. The lipid-film solubilization method is modified from the detergent dialysis method, which was described by Laukkanen M L, et al., (Laukkanen M L, et al., *Biochemistry* (1994) 33:11664-11670) and de Kruif et al., (de Kruif et al., *FEBS Lett*. (1996) 399:232-236) for neutral or anionic liposomes, with the methods of both hereby incorporated by reference. This method is suitable for attaching lipid-tagged scFv to cationic liposomes as well. In the lipid-film solubilization method, the lipids in chloroform are evaporated under reduced pressure to obtain a dry lipid film in a glass round-bottom flask. The lipid film is then solubilized with 0.54%, preferably 1%, n-octyl β-D-glucoside (OG) containing the lipid-modified scFv and vortexed. After dilution with sterile water, the solution is briefly sonicated to clarity.

The second method for attaching lipid-tagged antibodies or antibody fragments is the direct anchoring method that is specifically useful for attaching the E coli lipoprotein N-terminal 9 amino acids to an scFv (lpp-scFv) or other lipid-modified antibody or fragments and attaching these to preformed liposomes. For attaching the scFv to preformed liposomes, the lipid-modified scFv in 1% OG is added to preformed liposomes while vortexing, at volume ratios from 1:3 to 1:10. The mixture is vortexed for approximately a further 5-10 minutes to obtain a clear solution of scFv-immunoliposomes. The remaining OG and the uncomplexed scFv can be eliminated by chromatography, although they will not interfere very much with the subsequent usage. Separation experiments, i.e., ultrafiltration with Centricon-100 (Amicon), Ficoll-400 floatation (Shen D F, et al., *Biochim. Biophys. Acta* (1982) 689: 31-37), or Sepharose CL-4B (Pharmacia) chromatography, demonstrated that virtually all the lipid-tagged scFv molecules added have been attached or anchored to the cationic liposomes. This is an improvement over the much lower attachment rate of lpp-scFv to neutral or anionic liposomes. Therefore, this improvement makes it unnecessary to include a further purification step to remove the unattached scFv.

Any antibodies, antibody fragments, or other peptide/protein ligands that can be modified to have one or more lipid-tags on the surface are useful in the present invention. Other lipid-modification methods include directly conjugating a lipid chain to an antibody or fragment, as described in *Liposome Technology*, 2nd Ed., Gregoriadis, G., Ed., CRC Press, Boca Raton, Fla., 1992.

In another aspect of the invention a cysteine was added at the C-terminus of the scFv sequence and the protein was expressed in the inclusion bodies of *E. coli*, then refolded to produce active scFv. The C-terminal cysteine provided a free sulfhydryl group to facilitate the conjugation of the scFv to liposomes. There are two strategies which can be used in the conjugation process. 1) Pre-linking method: The first step is to conjugate the scFv-SH with the cationic liposome which contains a maleimidyl group or other sulfhydryl-reacting group, to make the scFv-liposome. The nucleic acids are then added to the scFv-liposome to form the scFv-liposome-DNA complex. The pre-linking is designated since scFv is linked before DNA complexing. 2) Post-linking method: This strategy is to complex the cationic liposome with nucleic acids first to form a condensed structure. The scFv-SH is then linked onto the surface of DNA-liposome complex to produce scFv-liposome-DNA. The post-linking is designated since scFv is linked after DNA complexing. The post-linking strategy ensures that 100% of scFv linked are on the surface of the complex, accessible to receptor binding. Therefore, this method can make a better use of the targeting ligand scFv and a better controlled inside structure of the complex.

The nucleic acid-immunoliposome complexes, regardless of whether the antibody or antibody fragment is lipid tagged or conjugated to the liposome, can be used therapeutically. Preferably the complexes are targeted to a site of interest, preferably to a cell which is a cancer cell, more preferably to a cell expressing a transferrin receptor. The targeting agent is the antibody or antibody fragment which preferably binds to a transferrin receptor. The nucleic acid is the therapeutic agent and is preferably a DNA molecule and more preferably encodes a wild type p53 molecule. The nucleic acid-immunoliposome complexes, preferably in a therapeutic composition, can be administered systemically, preferably intravenously.

DETAILED DESCRIPTION OF THE INVENTION

The invention is directed to immunoliposomes and methods of making and using these immunoliposomes. A variety of embodiments are disclosed including immunoliposomes with different tags and various methods with which to attach the scFv to the liposomes. The immunoliposomes may include lipid tags or be linked through a reducing group, which in a preferred embodiment is a free sulfhydryl.

Mutant forms of the tumor suppressor gene p53 have been associated with more than 50% of human cancers, including 15-50% of breast and 25-70% of metastatic prostate cancers. Abnormalities in p53 also correlate with poor prognosis in various types of malignancies. Therefore, the capability to systemically deliver and target gene therapy specifically to tumors to efficiently restore wtp53 function will be an important therapeutic modality in cancer treatment. Thus the immunoliposomes produced by the method of this invention will be useful as an effective new cancer therapeutic modality not just for restoration of wtp53 function but also as a tumor targeted systemic delivery vehicle for other therapeutic genes.

The invention is illustrated by the following Examples.

EXAMPLE 1

Construction and Expression of Biosynthetically Lipid-Tagged scFv

1. Construction of the Expression Vector for TfRscFv

Figure 1:
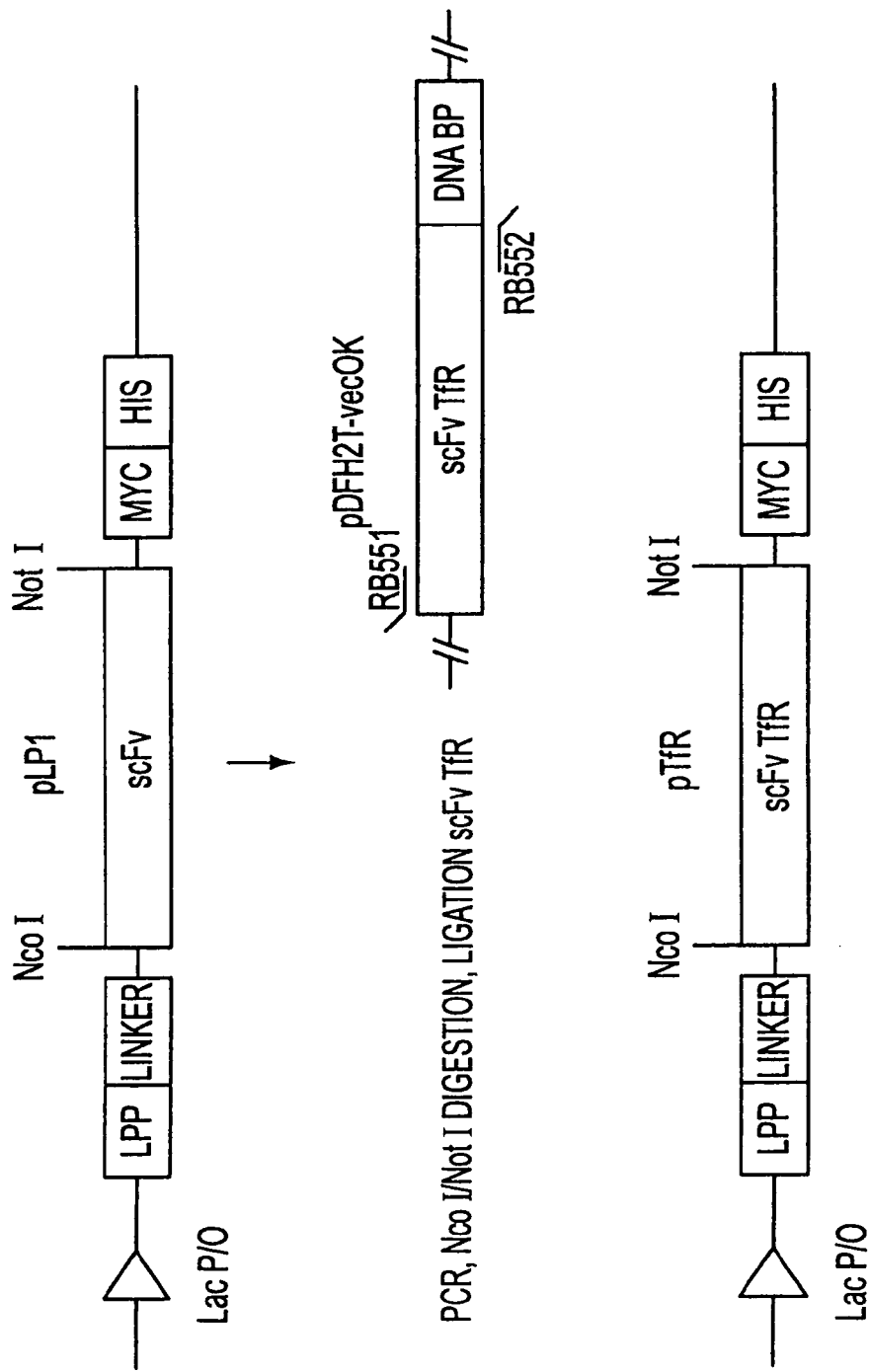
FIG. 1 show scFv TfR lipid-tag construction.

To construct the expression vector, we used the vector pLP1 which contains an amino acid linker sequence between the *E. coli* lipoprotein signal peptide (ssLPP) and the scFv cloning site (de Kruif et al., *FEBS Lett.* (1996) 399:232-236). This vector contains both c-myc and $His_6$ tag sequences that can be used for purification and detection of the expressed scFv (FIG. 1).

We obtained a plasmid expression vector, pDFH2T-vecOK, which contains the single chain fragment for the 5E9 (Haynes et al., *J. Immunol.* (1981) 127:347-351) antibody linked to a DNA binding protein, which recognizes the human transferrin receptor (TfR). This vector also contains the sequence for a DNA binding protein, and there are no unique restriction enzyme sites flanking the scFv sequence in pDFH2T-vecOK. Therefore, we cloned the VH-linker-Vκ scFv by PCR amplification of the desired fragment using a 5' primer (5' GGCCCATGGAGGTGCAGCTGGTGG 3' (SEQ ID NO:1)) (RB551) containing an NcoI site and a 3' primer (RB552) (5' CCGGAATTCGCGGCCGCTTTTATCTC-CAGCTTGGTC 3' (SEQ ID NO:2) containing a NotI site. The PCR amplification using primers RB551 and RB552 amplified the scFv for TfR from pDFH2T-vecOK from the Met at base 81 to Lys at base 821. The pLP1 vector also contains sequences for the *E. coli* lipoprotein signal peptide (ssLPP) and the *E. coli* lipoprotein N-terminal 9 amino acids (LPP), as described by Laukkanen M L, et al., (Laukkanen M L, et al., *Biochemistry* (1994) 33:11664-11670) and de Kruif et al (de Kruif et al., *FEBS Lett.* (1996) 399:232-236). The insertion of these sequences will lead to fatty acid acylation of the expressed signal in the *E. coli* host and its insertion into the bacterial membrane. The vector also has a non-critical 10 amino acid linker sequence to increase the space between the lipid-tag site and the scFv. Purification of the lipid modified scFv sequence from the bacterial membrane results in an active molecule that can be attached or inserted into liposomes.

2. Expression and Purification of the TfRscFv

We transformed *E. coli* expression host SF110 F' with the expression vector constructed above. While the host cell is not critical it is preferred that it contain expressed lac repressor. A number of clones were selected and the one that produces the best yield of scFv was chosen. The lipid-modified scFv (lpp-scFv) was isolated from the bacterial membrane using Triton X-100 as described by de Kruif et al., (de Kruif et al., *FEBS Lett.* (1996) 399:232-236). For purification a single colony was resuspended in 200 µl LB containing 5% glucose and the appropriate antibiotics. The mixture was plated onto two 90 mm LB agar plates containing 5% glucose and the appropriate antibiotics and grown overnight. The next day, the cells were washed from the plates and used to inoculate a total of 5 liters of LB containing 0.1% glucose and the appropriate antibiotics. The cultures were grown at 25° C., at 200 rpm for 6 hours until the $OD_{6000}$ reached 0.5 to 0.7. IPTG was added to a final concentration of 1 mM and the cultures were further incubated overnight. The next day, the bacterial cultures were collected by centrifugation and lysed in 200 ml lysis buffer at room temperature for 30 minutes. The sample was sonicated at 28 watts for 5 minutes with cooling on ice. The lysis buffer contains 20 mM HEPES pH 7.4 to 7.9, 0.5 M NaCl, 10% glycerol. and 0.1 mM PMSF. The only deviations from the cited protocol include washing and elution of metal affinity columns in buffer containing 20 mM HEPES pH 7.4 to 7.9, 0.5 M NaCl, 10% glycerol, 0.1 mM PMSF. 1% n-octyl β-D-glucoside (OG), and 10% glycerol containing 20 and 200 mM imidazole, respectively. The eluted samples of lpp-scFv were analyzed by SDS-PAGE and Western Blot using anti-c-myc antibody 9E10 which confirmed that the purified scFv showed a band of the size of about 30 kDa.

EXAMPLE 2

Preparation of Lipid-Tagged scFv-Immunoliposomes by a Lipid-Film Solubilization Method This example discloses a detailed procedure of lipid-film solubilization method to prepare lipid-tagged scFv-immunoliposomes. 5 μmol lipids (DOTAP/DOPE, 1:1 molar ratio) in chloroform are evaporated under reduced pressure to obtain a dry lipid film in a glass round-bottom flask. To the lipid film is added 0.5 ml 1% OG, 20 mM HEPES, 150 mM NaCl, pH 7.4, containing the lipid-modified scFv. This is incubated 10-20 minutes at room temperature and then vortexed to solubilize the lipid membrane. 2 ml sterile water is then added to dilute the scFv-lipid mixture. The solution is briefly sonicated to clarity in a bath-type sonicator at 20° C. The scFv-liposome is a clear solution with a limited amount of detergent OG left. The OG aid the uncomplexed scFv can be eliminated by chromatography with Sepharose CL-4B or Sephacryl S500, even though they do not interfere a lot with the subsequent use.

EXAMPLE 3

Preparation of Lipid-Tagged scFv-Immunoliposomes by a Direct Anchoring Method

This example provides a direct anchoring method to prepare lipid-tagged scFv-immunoliposomes. 20 μmol lipids (LipA-H, see below for compositions and ratios) prepared as dry lipid film in a glass round-bottom flask is added to 10 ml pure water and sonicated in a bath-type sonicator for 10-30 min at room temperature (LipA, B, C) or at 65° C. (LipD, E, G, H, or any composition with Cholesterol (Chol)). The cationic liposomes prepared are clear solutions, their compositions and ratios are as follows:

| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

For attaching the scFv to preformed liposomes, the lipid-modified scFv (lpp-scFv) in 20 mM HEPES, 150 mM NaCl, pH 7.4, containing 1% OG is added to preformed liposomes while vortexing, at volume ratios from 1:3 to 1:10. The mixture is vortexed for a further 1 to 5 min to get a clear solution of scFv-immunoliposomes. The remaining OG and the uncomplexed scFv can be eliminated by chromatography although they do not interfere very much with the subsequent usage. Separation experiments, i.e., ultrafiltration with Centricon-100 (Amicon), Ficoll-400 floatation (Shen D F, et al., *Biochim Biophys Acta* (1982) 689:31-37), or Sepharose CL-4B (Pharmacia) chromatography, demonstrated that virtually all the lipid-tagged scFv added have been attached or anchored to the cationic liposomes. This is in contrast to the much lower attachment rate of lpp-scFv to neutral or anionic liposomes. Therefore, it is unnecessary to have a further purification step to get rid of the unattached scFv.

EXAMPLE 4

Immunoreactivity of Lipid-Tagged scFv-Immunoliposomes Revealed by ELISA, FACS and Immunofluorescence This example provides the characterization of the anti-TfR scFv-immunoliposomes with respect to their ability of binding to the TfR(+) cells. The human prostate cancer cell line DU145 and the human squamous cell carcinoma of head and neck cell line JSQ-3 served as the TfR+ target cells for these studies.

Indirect cellular enzyme-linked immunosorbent assay (ELISA) was employed to determine the immunoreactivity of the lpp-scFv before and after attachment to liposomes. Confluent JSQ-3 cells in 96-well plates were fixed with 0.5% glutaraldehyde in PBS for 10 min at room temperature. The plate was blocked with 5% fetal bovine serum (FBS) in PBS at 30° C. for 30 min. The lpp-scFv, scFv-immunoliposomes and liposomes were added to wells in duplicate and incubated at 4° C. overnight. After three PBS-washes, an anti-c-myc monoclonal antibody was added to each well in 3% FBS in PBS and incubated at 37° C. for 60 min. After three PBS-washes, HRP-labeled goat-anti-mouse IgG (Sigma) diluted in 3% FBS was added to each well and incubated for 30 min at 37° C. The plate was washed three times with PBS and 100 μl substrate 0.4 mg/ml OPD in citrate phosphate buffer (Sigma) was added to each well. The color-development was stopped by adding 100 μl 2 M sulfuric acid to each well. The plate was read by an ELISA plate reader (Molecular Devices Corp.) at 490 nm. Indirect cellular ELISA demonstrated that the anti-TfR scFv retained its immunoreactivity after incorporation into the to liposome complex (Table 1).

TABLE 1

| Binding of anti-TfR scFv-liposomes to JSQ-3 cells* | |
| --- | --- |
| Lip(A) only | 0.142 ± 0.036 |
| scFv-LipA1 | 1.134 ± 0.038 |
| scFv-LipA2 | 1.386 ± 0.004 |
| lpp-scFv | 0.766 ± 0.009 |

*ELISA, $OD_{490}$, Mean ± SD
scFv-LipA1: by lipid-film solubilization method.
scFv-LipA2: by direct anchoring method.

For FACS analysis, anti-TfR scFv-Lip(A), was incubated at 4° C. with JSQ-3 and DU145 cells, then with FITC-labeled sheep anti-mouse IgG, also at 4° C. Incubation of JSQ-3 cells with the scFv-Lip(A) resulted in a fluorescence shift identical to that observed with the unattached free anti-TfR lpp-scFv antibody demonstrating a significant amount of binding to the target cells. In contrast, the untargeted liposome demonstrated very low binding to the cells. Similar results were observed with prostate tumor cell line DU145. Here also, the scFv-Lip(A) complex demonstrated clear, substantial binding to the tumor cells as compared to the untargeted Lip(A). The FACS data is summarized in Table 2, where the fluorescence shift is indicated as the percent of the cells displaying fluorescence above the threshold level (percent of positive cells). In these studies also, the level of binding to the cells, represented by the percent of positive cells, was similar to that of the unattached free scFv further indicating that incorporation into the liposome complex did not inactivate the immunological activity of the anti-TfR lpp-scFv. It should be noted that the liposome preparation used for these initial experiments with DU145 was that optimized for JSQ-3 cells. Therefore, the binding of the scFv-targeted liposome complex to the prostate tumor cells can be further enhanced by the use of the liposome complex optimized for this cell type.

TABLE 2

FACS Analysis of TfRscFv-liposome Binding to JSQ-3 and DU145

| Transfected by | JSQ-3 | | DU145 | |
|---|---|---|---|---|
| | % Positive | Mean[a] | % Positive | Mean[a] |
| Untransfected | 3.46 | 4.07 | 2.22 | 3.40 |
| Lip(A) | 9.69 | 6.26 | 4.51 | 4.07 |
| scFv-LipA1 | 86.38 | 19.8 | 50.19 | 12.40 |
| scFv-LipA2 | 89.58 | 21.30 | 39.52 | 11.1 |
| Free lpp-scFv | 85.09 | 21.30 | 78.09 | 18.40 |
| HB21[b] | 99.44 | 69.80 | 98.70 | 64.90 |

[a]Mean of the relative fluorescence
[b]Parental monoclonal antibody of the anti-TfR scFv Indirect immunofluorescence staining with scFv-liposome (where Lip(A) had been labeled with rhodamine-DOPE) and FITC-labeled anti-mouse IgG following anti-c-myc antibody, confirmed the binding of the scFv-targeted liposome complex to the JSQ-3 cells. The concurrence of the red and green fluorescence in the transfected cells demonstrates that the anti-TfR scFv (indicated by the FITC-labeled anti-c-myc antibody as green fluorescence) does indeed direct the rhodamine-labeled Lip(A) to the cells. Moreover, the high level of cellular binding of the scFv-Lip(A) system is demonstrated by the large percentage of red/green double-positive fluorescent cells.

EXAMPLE 5

Figure 3:
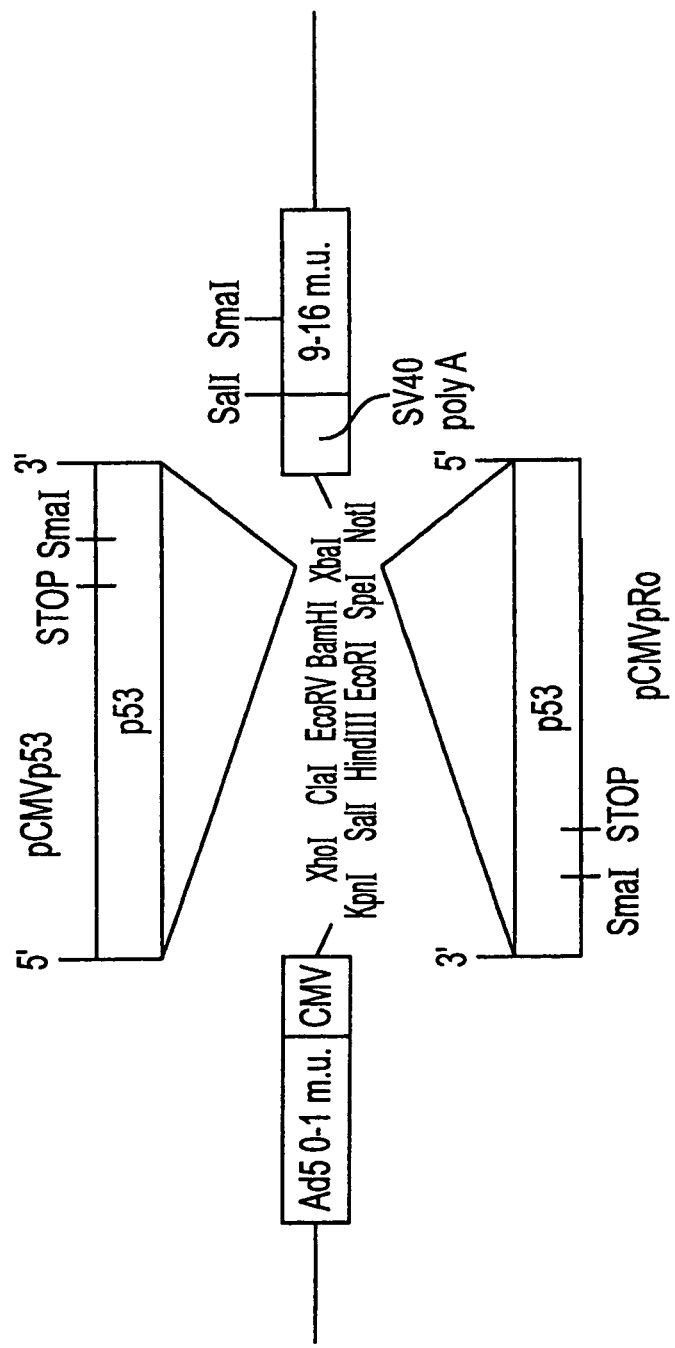
FIG. 3 shows pCMVp53 and pCMVpRO constructs.

Optimization of scFv-Immunoliposome Mediated Gene Transfection of Target Cells In Vitro We determined the in vitro transfection efficiency of the anti-TfR scFv-Lip(A) complex in JSQ-3 cells using β-galactosidase as the reporter gene. In these studies the reporter construct used contained the β-galactosidase gene under the control of the CMV promoter (pCMVb), the same promoter used in pCMVp53 (FIG. 3). The level of β-Gal expression in the transfected cells (correlating with the transfection efficiency) was assessed by β-Gal enzymatic assay (Xu L, et al., Hum. Gene Ther. (1997) 8:467-475). As shown in Table 3, the attachment of the anti-TfR scFv to the Lip(A) resulted in a doubling of the enzyme activity in the scFv-Lip(A)-pCMVb transfected cells, as compared to the untargeted liposome complex. This level of expression was also found to be virtually identical to that observed when transferrin itself was used as the targeting ligand (Tf-Lip(A)-pCMVb). Moreover, this increase in gene expression was shown to be reporter gene DNA dose dependent. Table 4 shows the optimization of scFv-liposome mediated transfection of JSQ-3 cells.

TABLE 3

Transfection of JSQ-3 Cells by Anti-TfR scFv-liposomes*

| DNA (µg/well) | Lip(A) only | Tf-Lip(A) | scFV-LipA1 | scFv-LipA2 |
|---|---|---|---|---|
| 1.0 | 475 | 1031 | 997 | 1221 |
| 0.5 | 601 | 981 | 811 | 854 |
| 0.25 | 266 | 503 | 578 | 471 |
| 0.125 | 130 | 262 | 215 | 236 |

*milliunits/mg protein, β-galactosidase equivalent, β-Gal enzymatic assay
scFv-LipA1: by lipid-film solubilization method
scFv-LipA2: by direct anchoring method

TABLE 4

Optimization of scFv-liposome transfection to JSQ-3*

| DNA/Lip (µg/nmol) | Lip(A) only | scFv-LipA1 | scFv-LipA2 | scFv-LipB | scFv-LipD | sFv-LipG |
|---|---|---|---|---|---|---|
| 1/8 | 1.559 | 2.793 | 2.642 | 1.827 | 0.874 | 0.648 |
| 1/10 | 1.776 | 2.846 | 2.83 | 2.268 | 1.606 | 1.283 |
| 1/12 | 1.868 | 2.772 | 2.815 | 2.175 | 1.257 | 1.416 |
| 1/14 | 1.451 | 3.031 | 2.797 | 2.31 | 1.78 | 1.656 |

*β-Gal enzymatic assay, $OD_{405}$
scFv-LipA1: by lipid-film solubilization method
scFv-LipA2: by direct anchoring method

EXAMPLE 6 scFv-Immunoliposome Mediated p53 Gene Transfection Target to Tumor Cells Causing Sensitization to Chemotherapeutic Agents 1. Anti-TfR scFv Facilitated Liposome-Mediated wtp53 Gene Transfection In Vitro The expression of exogenous wtp53 in JSQ-3 tumor cells transfected with the anti-TfR scFv-targeted Lip(A)-p53-3!Ad was assessed by co-transfection of an expression plasmid (pBP100) which contains the luciferase reporter gene under the control of a p53 responsive promoter (Chen L, et al., Proc. Natl. Acad. Sci. USA (1998) 95:195-200). Consequently, the higher the level of exogenous wt p53 expression (representing the scFv-Lip(A)-p53-3'Ad transfection efficiency), the higher the level of luciferase activity. This luciferase enzyme activity is expressed as relative light units (RLU). As was demonstrated above with the β-gal reporter gene, the addition of the anti-TfR scFv as the targeting agent to the Lip(A)-p53-3'Ad complex resulted in a significant increase in transfection efficiency and wtp53 protein expression (as expressed by RLU of Luciferase activity) over the untargeted Lip(A)-p53-3'Ad complex (Table 5). Once again, the level of p53 expression in the scFv-Lip(A)-p53-3'Ad transfected cells was similar to that observed when transferrin itself was used as the targeting ligand (LipT(A)-p53-3'Ad). Therefore these findings indicate that the anti-TfR single-chain antibody strategy is a useful method of targeting the cationic liposome complex, and delivering a biologically active wtp53 gene, to tumor cells.

TABLE 5

In Vitro p53 Expression Mediated by Different Liposomes in JSQ-3 cells

| Transfected by | RLU* |
|---|---|
| Medium + p53-3'Ad + pBP100 | 158 |
| Lip(A) + p53-3'Ad + pBP100 | 4073 |
| LipT(A) + p53-3'Ad + pBP100 | 7566 |
| scFv-Lip(A1) + p53-3'Ad + pBP100 | 6441 |

*Relative light units per well

2. Anti-TfR scFv-Immunoliposome Mediated p53 Gene Restoration Sensitized the Tumor Cells to the Cytotoxicity of Cisplatin (CDDP).

Figure 4:
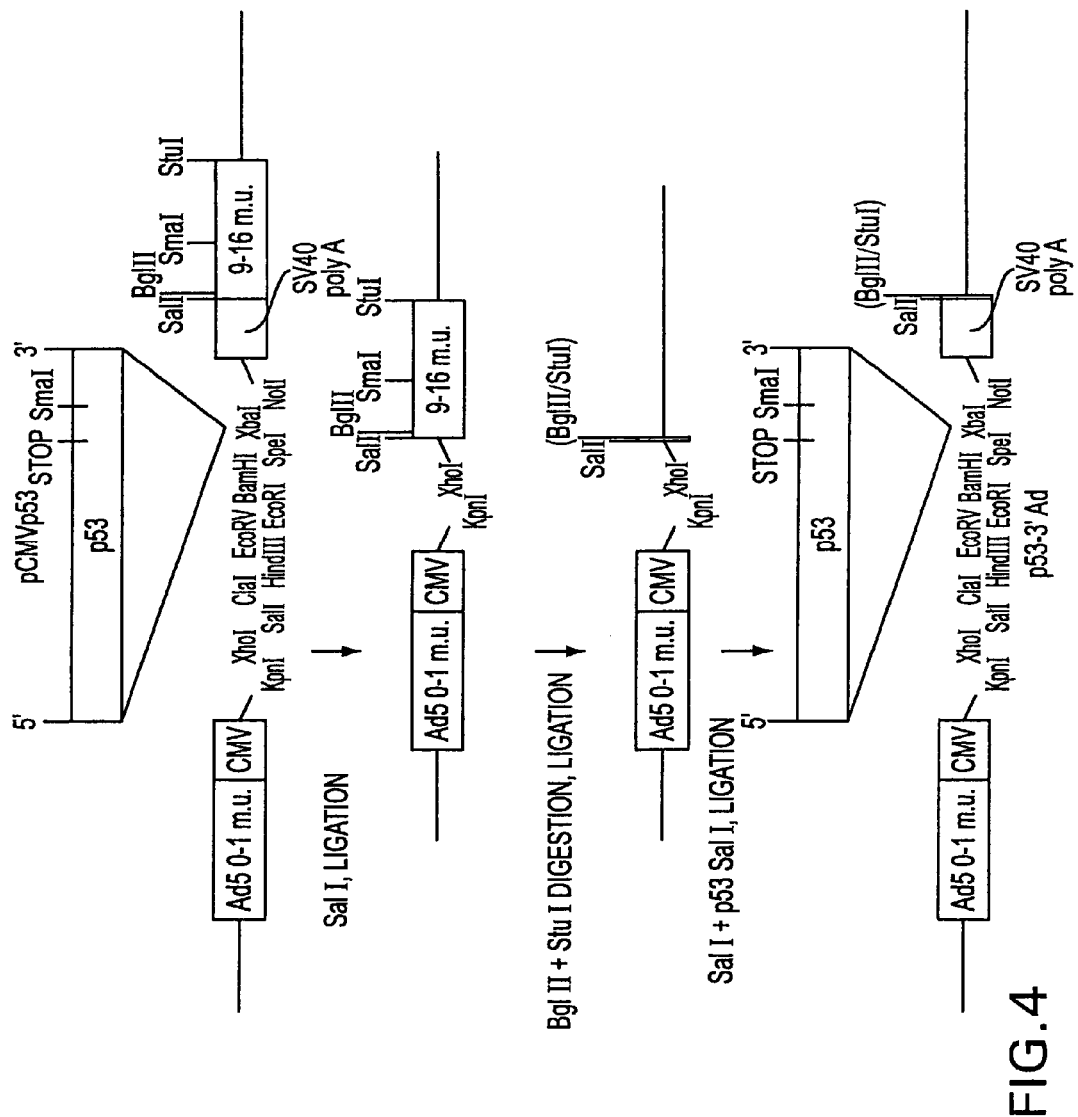
FIG. 4 shows p53-3'Ad construction.

For the p53-induced apoptosis study, mouse melanoma cell line B16 was transfected with anti-TfR scFv-immunoliposome complexed with p53-3'Ad (FIG. 4) or pCMVpRo plasmid (FIG. 3) DNA (scFv-Lip(A)-p53 and scFv-Lip(A)-pRo, respectively) at a dose of 5 µg DNA/2×10⁵ cells in 2 sets of 6-well plates. For comparison, transferrin-liposome-DNA (LipT-p53 or LipT-pRo) were also transfected at a dose of 5

μg DNA/2×10⁵ cells. 24 hours later, CDDP was added to one set of plates to 10 μM final concentration. 24 and 48 hours after the drug was added, both the attached and floating cells were collected for apoptosis staining. The cells were stained with an Annexin V-FITC Kit (Trevigen, Inc., Gaithersburg, Md.) according to manufacturer's protocol. Annexin V is a lipocortin, a naturally occurring blood protein and anti-coagulant. The stained cells were analyzed on a FACStar cytometer (Becton and Dickinson). Table 6 summarizes the results of the apoptosis analysis.

TABLE 6

Apoptosis of B16 Cells Induced by Liposomal p53-gene Restoration and CDDP*

| Transfected by | 24 hours | | 48 hours | |
| --- | --- | --- | --- | --- |
| | −CDDP | +CDDP | −CDDP | +CDDP |
| Untransfected | 0.22 | 4.4 | 6.33 | 20.11 |
| LipA-p53 | 15.9 | 26.7 | 15.02 | 26.52 |
| scFv-LipA-p53 | 13.9 | 38.4 | 34.94 | 43.7 |
| scFv-LipA-pRo | 8.1 | 19.9 | 24.14 | 37.59 |
| Tf-LipA-p53 | 22.4 | 29.5 | 34.47 | 31.7 |
| Tf-LipA-pRo | 14.1 | 12.6 | 14.00 | 25.34 |

*% of apoptotic cells (Annexin V-FITC positive)

Without CDDP there was no increase in the percent of apoptotic cells induced at 24 hours by the addition of the scFv ligand as compared to the amount induced by the liposome complex alone. However, by 48 hours, there is a greater than 2-fold increase in the percent of apoptotic cells by the addition of the targeting scFv to the lipoplex. With CDDP there is a significant increase in apoptotic cells (approximately 1.5-fold) even at 24 hours as compared to the untargeted liposome complex. More significantly, this increase in apoptotic cells in combination with CDDP is more pronounced using the scFv to the Tf receptor as the targeting ligand than using the Tf molecule itself This increase correlates with transfection efficiency.

Figure 2:
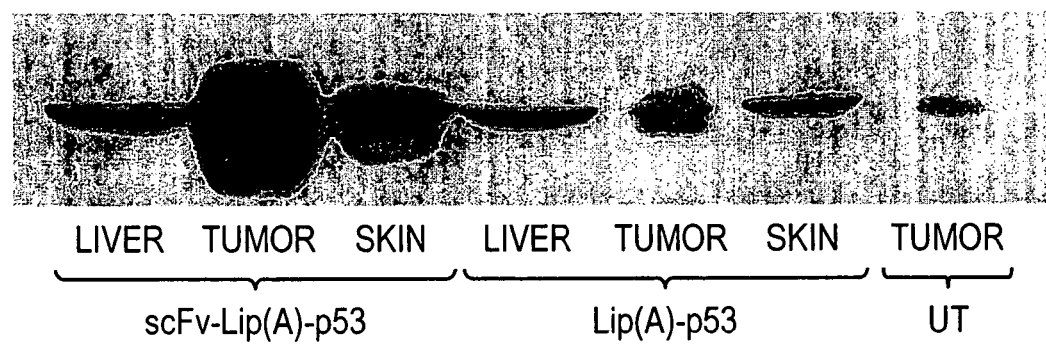
FIG. 2 shows a Western blot analysis of scFv-liposome-targeted p53 expression in vivo in tumor xenografts with systemic administration.

EXAMPLE 7 scFv-Immunoliposome-Targeted wtp53 Gene Delivery and Expression In Vivo with Systemic Administration To examine the ability of the anti-TfR scFv containing liposomes to deliver wtp53 specifically to tumor tissue in vivo, scFv-Lip(A)-p53-3'Ad (FIG. 4) or the untargeted Lip (A)-p53-3'Ad (FIG. 4) was injected intravenously into nude mice bearing JSQ-3 subcutaneous xenograft tumors. Two days after injection, the tumors were excised and protein isolated from liver and skin, as well as the tumor, for Western blot analysis (Xu L, et al., *Hum. Gene Ther*. (1997) 8:467-475). Equal amounts of protein (100 μg, as determined by concentration) were loaded in each lane. As shown in FIG. 2, the tumor from the mouse systemically treated with the scFv-Lip(A)-p53-3'Ad complex, labeled scFv-Lip(A)-p53 in FIG. 2, displayed a very intense p53 signal as well as the additional lower band indicative of a high level of expression of the exogenous wtp53, while only the lower expression of the endogenous mouse p53 is evident in both the skin and the liver. In contrast, as would be expected based upon our earlier results, a significantly lower level of exogenous p53 expression is evident in the tumor isolated from the untargeted Lip(A)-p53-3'Ad injected mouse, labeled Lip(A)-p53 in FIG. 2. Therefore, the liposome complex targeted by our new and unique anti-TfR lpp-scFv ligand can clearly deliver exogenous genes selectively to the tumor in vivo. These results demonstrate the potential of this new way of efficiently targeting systemically delivered, cationic liposome complexes specifically to tumors in vivo.

EXAMPLE 8

Figure 5:
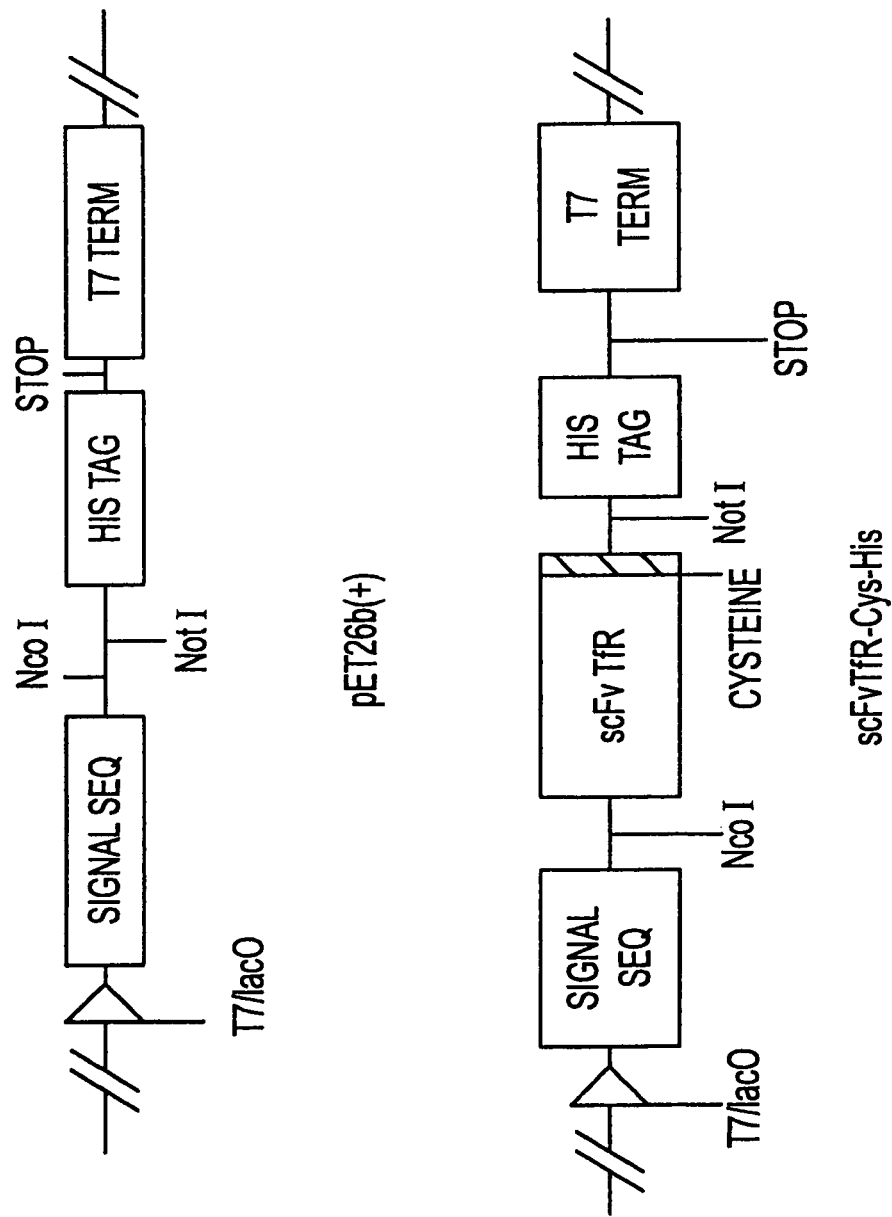
FIG. 5 shows construction of scFvTfR-cysteine with a His tag.
Figure 6:
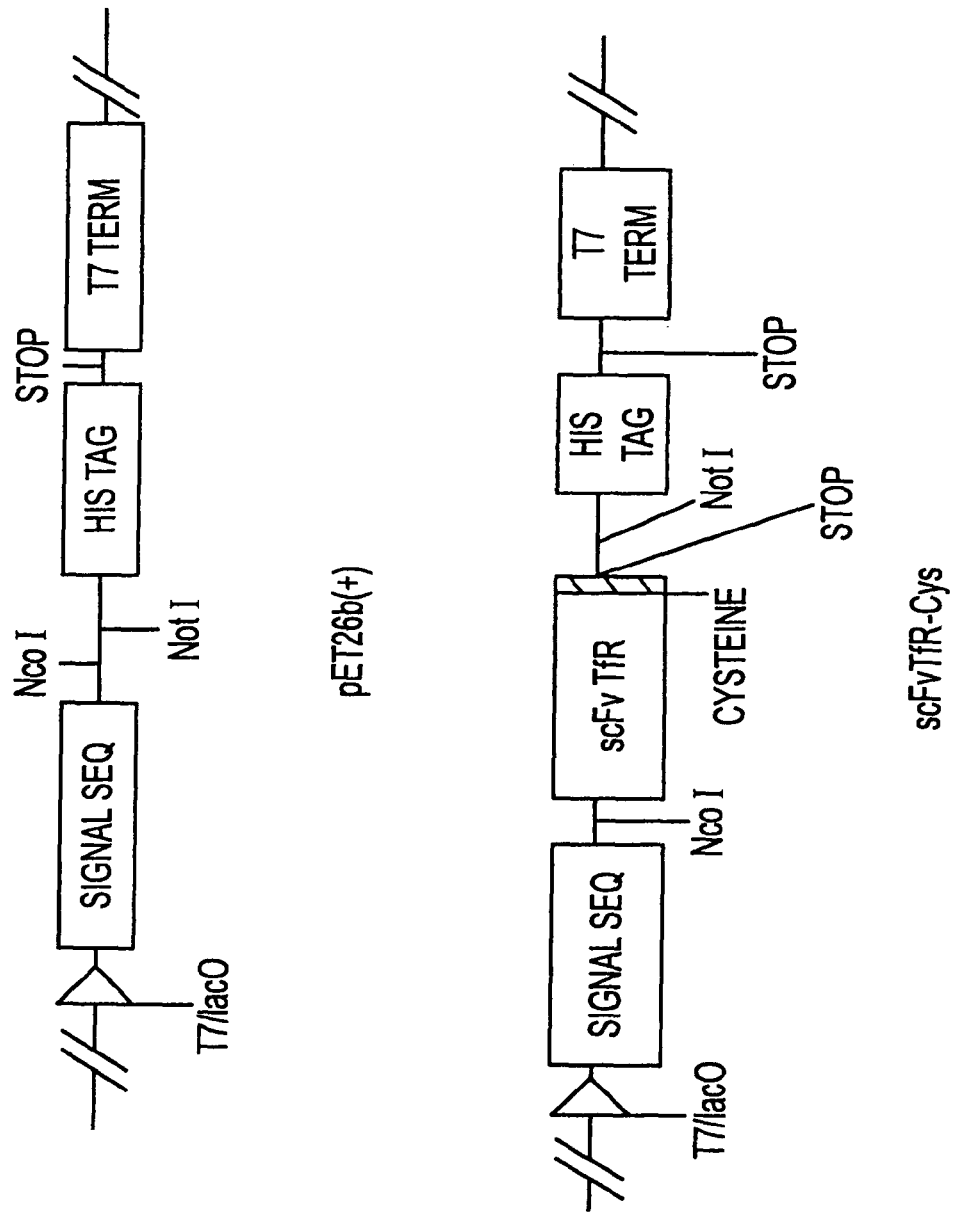
FIG. 6 shows construction of scFvTfR-cysteine without a His tag.
Figure 7:
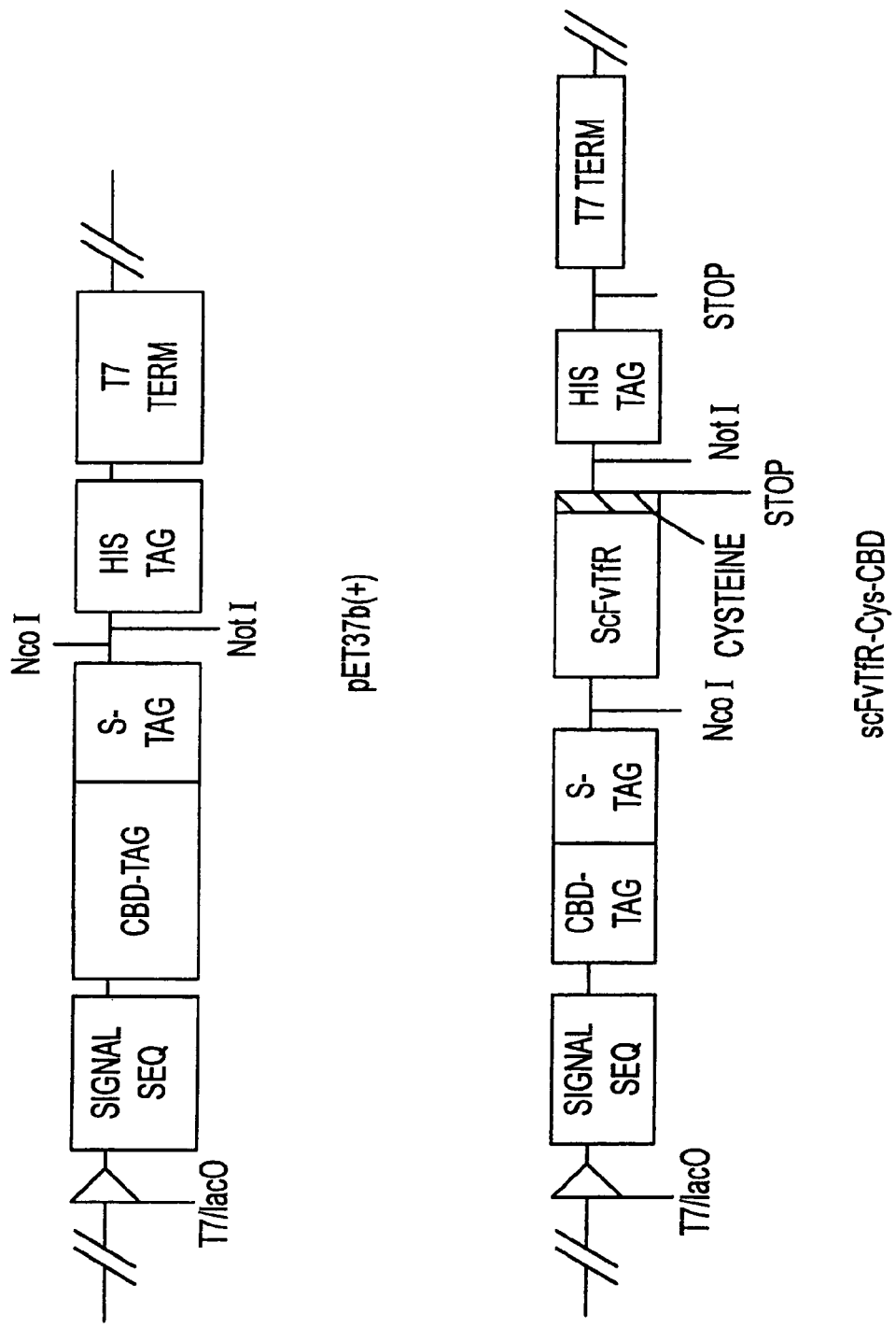
FIG. 7 shows construction of scFvTfR-cysteine with a cellulose binding domain (CBD) tag and with an S-tag.

Construction and Purification of TfRscFv with a 3' Cysteine for Use in the Conjugation Method In the absence of a lipid tag, another method was devised to attach the purified TfRscFv protein to the lipoplex. This approach entails the conjugation of the single chain protein to cationic liposomes via a reducible group such as a sulfhydryl group. In the preferred embodiment a cysteine residue is added at the 3' end of the TfRscFv protein. Reduction of this cysteine results in a free sulfhydryl group which is capable of being conjugated to cationic liposomes, thus targeting the lipoplex to cells expressing the transferrin receptor. While the following examples use cysteine as the reducible group it is obvious that other similar reducing groups would also work with this method.
1. Construction
A. Construction of an Expression Vector Containing a 3' Cysteine with a Histidine Tag for Use in the Conjugation Method of Producing TfRscFv Immunoliposomes As in Example 1, the VH-linker-Vκ scFv for the TfR was obtained from plasmid expression vector, pDFH2T-vecOK (described in Example 1). Using a 5' primer (5' GGCCCATG-GAGGTGCAGCTGGTGG 3' (SEQ ID NO:3)) for PCR amplification, an NcoI site was introduced into pDFH2T-vecOK. The nucleotide sequence for the cysteine residue as well as a NotI restriction site was introduced using a 3' primer (5' GGCGCGGCCGCGCATTTTATCTCCAGCTTG 3' (SEQ ID NO:4)). The PCR product was cloned into NcoI and NotI sites of the commercial vector pET26b(+) (Novagen). This vector also contains, 5' of the NcoI site, the pelB leader signal sequence. The presence of this sequence in the expression vector allows transport of the protein to the periplasmic space. To aid in purification of the protein, the pET26b(+) vector also contains a Histidine tag sequence 3' of the NotI site (FIG. 5).
B. Construction of an Expression Vector Containing a 3' Cysteine without a Histidine Tag for Use in the Conjugation Method of Producing TfRscFv Immunoliposomes For human use as a therapeutic delivery vehicle, it is preferable that the TfRscFv be produced without the Histidine tag. Therefore, the construct described in Example 8, section 1. A, was modified to eliminate this tag in the final protein product. To accomplish this, the same 5' primer as described above (in Example 8, section 1. A) was used. However, a different 3' primer was used. In addition to the nucleotide sequence for the cysteine residue and the NotI restriction site, this primer (5'GGCGCGGCCGCTCAGCATTTTATCTC-CAGCTTG 3' (SEQ ID NO:5)), introduced a DNA stop codon adjacent to the cysteine sequence and before the NotI site (FIG. 6). Thus, the protein product of this construct will not contain the His-tag.
C. Construction of an Expression Vector Containing a 3' Cysteine with a 5' CBD™-Tag for Use in the Conjugation Method of Producing TfRscFv Immunoliposomes A third alternative construct containing a cysteine residue for linkage to the cationic lipoplex using the conjugation method was also made. For this construct (FIG. 7), the same two primers described above in Example 8, section 1 B, were used. Thus no His-tag would be present in the protein product.

However, the PCR product of these reactions was cloned into a different vector, pET37b(+) (Novagen). This vector contains a cellulose binding domain tag (CBD™-tag) and an S-tag, both 5' of the NcoI site in the vector. The CBD-tag sequence encodes a cellulose binding domain derived from a microbial cellulase. Thus, the presence of this tag enables the use of cellulose-based supports for highly specific, low cost affinity purification of the protein product. The presence of the S-tag present in this construct allows for easy detection of the protein product on Western blots and for easy enzymatic quantitation of protein amounts.

2. Purification of the TfRscFv Containing the Cysteine Residue

The commercially available *E. coli* expression host BL21 (DE3), which contains the expressed lac repressor, was transformed with an expression vector (all three were used individually) described above in Example 8, section 1. A number of clones were selected and the ones that produced the best yield of TfRscFv were chosen. Purification of the protein from the construct described above in Example 8. section 1. A, with the histidine tag is given in detail as an example, although the same method is used for purification of the cysteine containing TfRscFv protein from all three constructs described in Example 8, section 1. The majority of the TfRscFv protein (approximately 90%) was found not to be soluble but to be contained within the inclusion bodies. Therefore, the TfRscFv containing the cysteine-linker was purified from the inclusion bodies as follows. A single clone was inoculated into 5-10 ml LB containing 50 µg/ml Kanamycin, and grown at 37° C., and 250 rpm to an $OD_{600}$ of 0.5-0.7 (4-5 hrs). 30 ml of the mini culture was pelleted, suspended in LB broth, added to 1 L LB containing 50 µg/ml Kanamycin and incubated at 37° C. and 250 rpm, to an $OD_{600}$ of 0.5-0.7 (4-5 hrs). To induce expression of the TfRscFv protein, IPTG at a final concentration of 1 mM was added to the culture at this time and incubation continued for an additional 4 hrs. This time was determined to yield the maximum level of protein expression. The bacterial cultures were then collected by centrifugation and lysed in 100 ml of cold 20 mM Tris-HCl, pH 7.5, containing 100 µg/ml lysozyme, at 30° C. for 15 minutes. The sample was sonicated at 1 0 watts for 5 minutes (in 30 second bursts) with cooling on ice. The inclusion bodies were isolated by centrifugation at 13,000 g for 15 minutes. The resulting pellet was washed three times in cold 20 mM Tris-HCl buffer, pH 7.5. The purity and quantity of the inclusion bodies were determined by SDS-polyacrylamide gel electrophoresis before solubilization.

Figure 8:
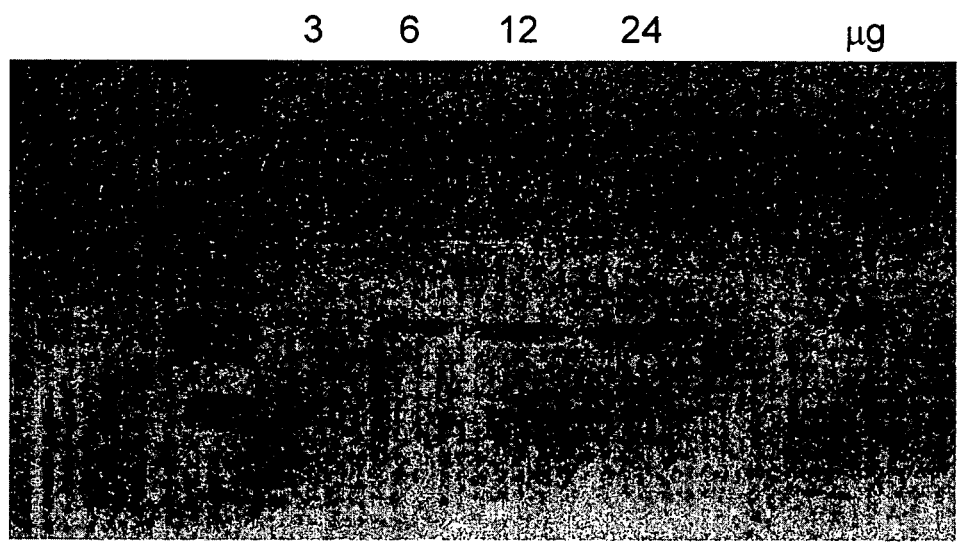
FIG. 8 shows a Coomassie Blue stained SDS-polyacrylamide gel of purified TfRscFv protein produced by the conjugation method.

The isolated inclusion bodies were dissolved in 100 mM Tris-HCl, pH 8.0 containing 6 M guanidine-HCl and 200 mM NaCl (6 M GuHCl buffer) and centrifuged at 12,300 g for 15 minutes to remove insoluble debris. 2-mercaptoethanol was added to the supernatant to a final concentration equal to approximately 50 molar fold of the protein concentration and the mixture incubated with rotation for 1 hour at room temperature. The presence of such a high concentration of guanidine-HCl and the reducing agent results in a totally unfolded protein. Refolding of the TfRscFv protein was accomplished by dialysis at 4° C. against decreasing concentrations of guanidine-HCl in the absence of 2-mercaptoethanol: Dialysis was performed for 24 hours each against the following concentrations of guanidine-HCl in 100 mM Tris-HCl, pH 8.0 and 200 mM NaCl: 6 M, 3 M, 2 M, 1 M and 0.5 M. The last dialysis was against three changes of just 100 mM Tris-HCl, pH 8.0 and 200 mM NaCl. The fourth dialysis solution (of 1 M guanidine-HCl) also contained 2 mM glutathione (oxidized form) and 500 mM L-arginine. These reagents allow the partially refolded protein to form the proper disulfide bonds to produce the correct protein conformation. The solution was clarified by centrifugation at 13000 g to remove aggregates. The sample was concentrated approximately 1.5 fold using the Centrplus centrifugal filter (Amicon) at 3000 g for 90 min. SDS-PAGE showed a single band of the solubilized cysteine containing TfRscFv with a molecular weight of approximately 28-30 kDa containing only minor contaminants (FIG. 8).

EXAMPLE 9

Preparation of scFv-Liposomes by the Conjugation Method

1. Reduction of scFv

The purified TfRscFv was reduced by DTT to obtain monomer scFv-SH as follows: To scFv in HBS (10 mM HEPES, 150 mM NaCl, pH 7.4) was added 1 M DTT to a final concentration of 1-50 mM. After rotation at room temperature for 5-10 min, the protein was desalted on a 10-DG column (Bio-Rad). The free —SH group was measured by 5,5'-dithiobis-(2-nitrobenzoic acid) (DTNB, Ellman's reagent) (G. L. Ellman (1959) *Arch. Biochem. Biophys.* 82:70-77. P. W. Riddles, R. L. Blakeley, B. Zeruer (1993) *Methods Enzymol.* 91:49-60) and calculated as —SH/protein molar ratio, or number of free —SH per scFv molecule (Table 7). The results indicate that 1-10 mM DTT is appropriate for the scFv reduction.

TABLE 7

| Reduction of TfRscFv | |
|---|---|
| DTT Concentration (mM) | -SH/scFv molar ratio |
| 0 | 0.15 |
| 1 | 0.45 |
| 10 | 1.94 |
| 20 | 2.26 |
| 50 | 3.03 |

2. Liposome Preparation 4-(p-maleimidophenyl)butyrate-DOPE (MPB-DOPE) (Avanti Polar Lipids) is included in the seven liposome formulations described in Example 3, to a 5-8% molar of total lipids. The MPB-liposomes were prepared the same way as described in Example 3. Other liposome preparation methods can also be used to prepare the cationic liposomes. For example, the ethanol injection method modified form that described by Campbell M J (*Biotechniques* June 1995; 18(6): 1027-32) was used successfully in the present invention. In brief, all lipids were solubilized in ethanol and mixed, injected into vortexing pure water of 50-60° C. with a Hamilton syringe. The solution was vortexed for a further 10-15 min. The final concentration was 1-2 mM total lipids. The ethanol injection method is faster, easier and more robust. 1 M HEPES, pH 7.5 (pH 7.0-8.0) was added to a final concentration of 10-20 mM. Since we have found that the maleimide group is not stable in aqueous solution with pH>7, the liposomes should be prepared in water (pH 5-6.5). The pH can be adjusted to 7.0-8.0 before linking to scFv-SH with 1 M HEPES buffer, pH 7.0-8.0. to facilitate the post-coating reaction.

3. Preparation of scFv-Liposome-DNA Complexes

A. Pre-linking Method scFv-SH was added to MPB-liposome at a protein/lipid (w/w) ratio of 1/5-1/40, preferably 1/10-1/20. The solution was mixed by gentle rotation for 30 min at room temperature to yield scFv-Lip. The scFv-Lip was used without purification although it can be purified by Sepharose CL-4B column chromatography. Plasmid DNA was diluted in water and added to the scFv-Lip at a DNA/lipid (μg/nmol) ratio of 1/6-1/20, preferably 1/10-1/14. The solution was mixed well for 5-15 min by inversion several times to produce scFv-Lip-DNA complex. scFv-Lip-DNA was used without purification although it can be purified by Sepharose CL-4B column chromatography. 80-100% of the scFv was found to be conjugated to the liposome.

B. Post-linking Method

Plasmid DNA was diluted in water and was added to the MPB-liposome at a DNA/lipid (μg/nmol) ratio of 1/6-1/20, preferably 1/10-1/14. The solution was mixed well for 5-15 min by inversion several times to produce an MPB-Lip-DNA complex. scFv-SH was then added to the complex at a protein/lipid (w/w) ratio of 1/5-1/40, preferably 1/10-1/20. The solution was mixed by gentle rotation for 30 min at room temperature, to produce the final scFv-Lip-DNA complex. The scFv-Lip-DNA was used without purification although it can be purified by Sepharose CL-4B column chromatography. 80-100% of the scFv was found to be conjugated to the liposome. 4. For intravenous injection, a 50% dextrose solution was added to the scFv-Lip-DNA to a final concentration of 5%.

EXAMPLE 10

Immunoreactivity of Cysteine Containing TfRscFv-Immunoliposomes by the ELISA Assay This example provides the characterization of the anti-TfRscFv-immunoliposomes produced by the conjugation method of this invention with respect to their ability to bind to TfR(+) cells in vitro. Human squamous cell carcinoma of head and neck cell line JSQ-3 served as the TfR(+) target cells for these studies.

As previously described in Example 4, indirect cellular enzyme-linked immunosorbent assay (ELISA) was employed to determine the immunoreactivity of the TfRscFv before and after conjugation to liposomes. Confluent JSQ-3 cells in 96-well plates were fixed with 0.5% glutaraldehyde in PBS for 10 min at room temperature. The plate was blocked with 5% fetal bovine serum (FBS) in PBS at 30° C. for 30 min. The cysteine containing TfRscFv alone, this TfRscFv conjugated to cationic liposomes (TfRscFv-immunoliposomes) and untargeted liposomes were added to wells in triplicate. An anti-transferrin receptor monoclonal antibody (Hb21, obtained from David Fitzgerald, NIH) was used in one series of wells as a positive control. The plate was incubated at 4° C. overnight. The wells were washed three times with PBS, and an anti-His monoclonal antibody (Qiagen) was added to each well (except for those receiving the antibody positive control) in 3% FBS in PBS and incubated at 37° C. for 60 min. After three PBS washes, HRP-labeled goat-anti-mouse IgG (Sigma) diluted in 3% FBS was added to each well and incubated for 30 min at 37° C. The plate was washed three times with PBS and 100 μl substrate 0.4 mg/ml OPD in citrate phosphate buffer (Sigma) was added to each well. The color-development was stopped by adding 100 μl 2 M sulfuric acid to each well. The plate was read on an ELISA plate reader (Molecular Devices Corp.) at 490 nm.

Indirect cellular ELISA clearly demonstrated that the anti-TfR scFv containing a C-terminal cysteine maintained its immunoreactivity. The $OD_{490}$ values increased with increasing amounts of TfRscFv protein, rising from 0.060±0.0035 with 0.6 μg of protein, to 0.100±0.0038 at 1.5 μg and 0.132±0.0031 with 3 μg of TfRscFv. Moreover, this TfRscFv protein appears to have even greater binding activity than the parental Hb21 anti-transferrin receptor antibody used as a positive control. The $OD_{490}$ for the highest concentration of the Hb21 (100 μl) was approximately 2-4 fold less (0.033±0.0086).

The indirect cellular ELISA assay was also performed after the same TfRscFv protein was incorporated via the conjugation method of the invention (Example 9) into two different liposome complexes (Lip(A) and Lip(B)) to demonstrate the universality of this method with cationic liposomes. Both the pre- and post-linking conjugation methods of liposome preparation detailed in Example 9 were used. As shown in Table 8, the immunoreactivity of the TfRscFv prepared by the conjugation method is not lost through complexing to either of the two liposome compositions. This was true for both pre- and post-linking methods used to produce the immunoliposome complex. The TfRscFv-targeted lipoplexes also demonstrated binding to the cells. This binding was significantly higher than that of the liposome without the TfRscFv, suggesting that this binding is in fact mediated through the attachment of the TfRscFv to the transferrin receptor on the cells.

TABLE 8

Binding of TfRscFv-immunoliposomes Prepared by the Conjugation Method to JSQ-3 Cells In Vitro*

| | DNA:Lipid Ratio | $OD_{490}$ |
|---|---|---|
| Lip(B)-DNA | 1:10 | 0.088 |
| TfRscFv-Lip(A)-DNA by Pre- | 1:10 | 0.152 ± 0.016 |
| TfRscFv-Lip(A)-DNA by Pre- | 1:12 | 0.166 ± 0.009 |
| TfRscFv-Lip(A)-DNA by Post- | 1:12 | 0.168 ± 0.006 |
| TfRscFv-Lip(B)-DNA by Pre- | 1:12 | 0.139 ± 0.012 |
| TfRscFv only | — | 0.235 |

*ELISA, $OD_{490}$, Mean ± SD (triplicate readings except for Lip(B)-DNA)
Pre- = Pre-linking Conjugation Method
Post- = Post-linking Conjugation Method

EXAMPLE 11

Conjugated TfRscFv-Immunoliposome Mediated Gene Transfection of Target Cells In Vitro We determined the in vitro transfection efficiency of the TfRscFv-liposome complex, prepared by the conjugation method, in cells using the plasmid pLuc, which contains the firefly luciferase gene under control of the CMV promoter as the reporter gene. To demonstrate the universality of the TfRscFv as a targeting ligand, here also, as in Example 10, two separate liposome compositions (Lip(A) and Lip(B)) were conjugated to the TfRscFv protein. Human breast cancer cell line MDA-MB-435 and human squamous cell carcinoma of the head and neck cell line JSQ-3 were used in these studies. The in vitro transfection was performed in 24-well plates (Xu L, et al., *Atom. Gene Ther.* (1999) 10:2941-2952). The transfection solutions were added to the cells in the presence of 10% serum. 24 hr later the cells were washed and lysed to measure the luciferase activity and protein concentration. The results are expressed as $10^3$ relative light units (RLU) per μg protein in the lysate, as shown in Tables 9A and 9B.

TABLE 9A

Conjugated TfRscFv-immunoliposome Mediated Transfection In Vitro[#]

| | Luciferase Activity ($\times 10^3$ RLU/µg protein) | |
|---|---|---|
| | MDA-MB-435 | JSQ-3 |
| LipA | 106 | 377 |
| Tf-LipA | 284 | 640 |
| scFv-LipA* | 560 | 1160 |
| scFv-LipA** | 660 | 1210 |
| scFv-LipA (1/10)[@] | — | 1315 |
| scFv-LipA (1/20)[@] | — | 751 |

[#]Mean of duplicates
*Containing 5% MPB-DOPE
**Containing 7% MPB-DOPE
[@]Ratio of scFv/lipids (w/w)

TABLE 9B

In Vitro Transfection Activity of Conjugated
TfRscFv-Immunoliposome-DNA Complexes
Prepared for Systemic Administration

| | Luciferase Activity ($\times 10^3$ RLU/µg protein) | |
|---|---|---|
| | MDA-MB-435 | JSQ-3 |
| scFv-LipA-pLuc (pre-linking)* | 58.4 | 675 |
| scFv-LipA-pLuc (pre-linking)** | 45.6 | 513 |
| scFv-LipB-pLuc (pre-linking)* | 51.4 | 415 |
| scFv-LipA-pLuc (post-linking)* | 58.1 | 856 |
| scFv-LipA-pLuc (post-linking)** | 45.3 | 343 |
| scFv-LipB-pLuc (post-linking)* | 47.2 | 237 |

*Containing 5% MPB-DOPE
**Containing 7% MPB-DOPE

The results show that the cysteine containing TfRscFv-immunoliposomes prepared by the conjugation method have very high transfection activity in vitro. 3-6 fold higher than the untargeted liposomes and 2-3 fold higher than the transferrin-targeted liposomes. This was true for both liposome compositions and both human tumor cell lines. Thus, they still retain their immunoreactivity and can bind to their target receptor. Based upon Table 9A, the scFv-liposomes can also be used as efficient gene transfection reagents in vitro and are much more efficient than commercially available cationic liposomes (DOTAP/DOPE and DDAB/DOPE) and transferrin-liposomes. The TfRscFv-immunoliposomes disclosed in the present invention can be used for an efficient in vitro gene transfection kit useful for the transfection of mammalian cells with transferrin receptors.

The TfRscFv is a smaller molecule than transferrin itself. Thus, the resulting complex is more compact and more easily taken up by the cells giving a higher transfection efficiency. These results are also advantageous for the use of the TfRscFv immunoliposome for systemic delivery for human use. The smaller size allows increased access to the tumor cells through the small capillaries. Most significantly, the TfRscFv is not a human blood product as is the Tf molecule. Therefore, the concerns and technical problems associated with the use of transferrin itself for human therapy are avoided.

EXAMPLE 12

Figure 9:
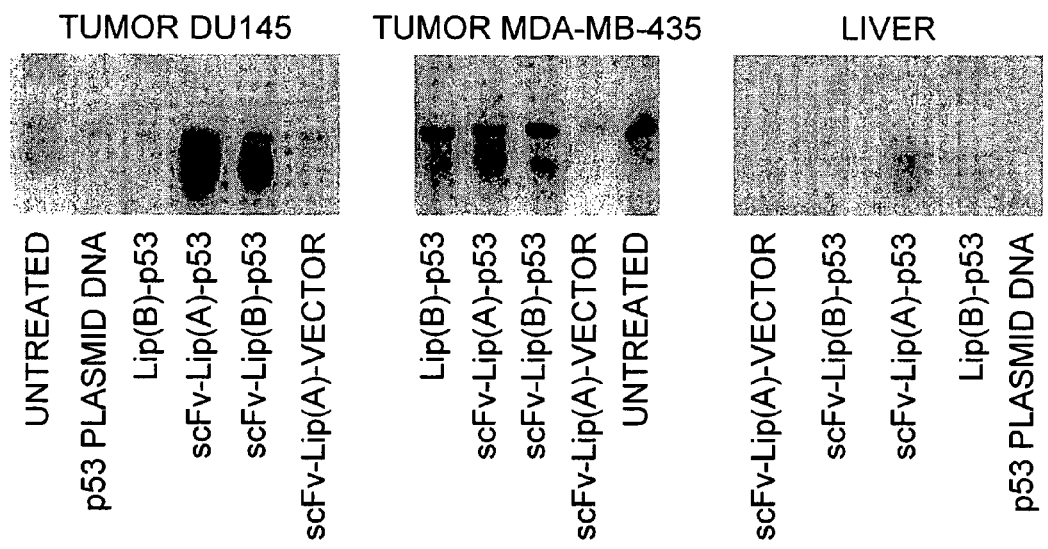
FIG. 9 shows a Western blot analysis of conjugation method produced TfRscFv-liposome-targeted p53 expression in vivo in tumor xenografts with systemic administration.

Conjugated TfRscFv-Immunoliposome Mediated
Expression of Wild-Type p53 in a Nude Mouse
Xenograft Model Following Systemic Delivery In this example the ability of the TfRscFv, produced by the conjugation method of this invention, to direct a lipoplex carrying the wild-type p53 (wtp53) gene preferentially to tumor cells in vivo after systemic delivery is demonstrated. To demonstrate the universality of the TfRscFv as a targeting ligand, here also, as in Example 10, two separate liposome compositions (Lip(A) and Lip(B)) were complexed to the cysteine-containing TfRscFv protein by the conjugation method. Only the pre-linking method of conjugation as detailed in Example 9 was used in this study. $2.5 \times 10^6$ MDA-MB-435 human breast cancer cells were subcutaneously injected into 4-6 wk old female athymic nude mice. $1.1 \times 10^7$ DU145 human prostate cancer cells suspended in Matrigel® collagen basement membrane (Collaborative Biomedical Products) were also subcutaneously injected into 4-6 week old female athymic nude mice and tumors were allowed to develop. Animals bearing tumors of between 50-200 mm$^3$ were used in the study (1 animal/sample tested). Conjugated TfRscFv immunoliposomes carrying the wtp53 gene, as well as untargeted Lip(B)-p53 and wtp53 naked DNA were intravenously injected into the tail vein of the animals. As an additional control, conjugated TfRscFv-Lip(A) carrying the empty vector in place of the p53 containing vector was also injected into a mouse. As described in Example 7, approximately 60 hours post-injection, the animals were sacrificed and the tumors, as well as the liver, were excised. Protein was isolated from the tissues and 100 µg of each sample (as determined by protein concentration assay) was run on a 10% polyacrylamide gel for Western blot analysis using an anti-p53 monoclonal antibody. In both of these tumor types the endogenous mouse and the exogenous human p53 migrate at the same position. The results here mirror those described in Example 7. As shown in FIG. 9, both the DU145 and MDA-MB-435 tumors from the animals intravenously injected with the TfRscFv-Lip(A)-pCMVp53 lipoplex or the TfRscFv-Lip(B)-pCMVp53 lipoplex prepared by the conjugation method displayed a high level of expression of exogenous wtp53, as indicated by the intense p53 signal and an additional lower band, with the best expression in the DU145 tumors. While it appears that in both tumor types the Lip(A) composition was somewhat better than the Lip(B), both liposome compositions worked demonstrating the universality of this method. Only the endogenous mouse p53 protein was evident in the liver of these animals. In contrast, only the endogenous mouse p53 protein was evident in the tumors excised from the mice injected with the conjugated TfRscFv-Lip(B) carrying the empty vector or the naked wtp53 DNA. A small increase in p53 expression also was observed in the DU145 tumor with the untargeted Lip(B)-p53. Thus, the conjugated TfRscFv-immunoliposomes delivered the wtp53 gene preferentially to the tumors, as desired. It is also significant that this tumor targeting was evident in two different tumor types, indicating the general usefulness of the method of this invention. Therefore, the methods of this invention described in the preceding Examples generate a TfRscFv protein that not only retains its ability to bind to cationic liposomes but is still immunologically active preserving its ability to bind to the transferrin receptor in vitro and in vivo, thus fulfilling our objective of producing a tumor-specific, targeted immunoliposome for gene therapy.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A plasmid construct for enhanced gene expression in mammalian cells, comprising, from 5' to 3':
   (a) human adenovirus 5 (Ad5) enhancer sequences present in map units 0-1 of Ad5, comprising two copies of Element I and a single copy of Element II;
   (b) a cytomegalovirus (CMV) promoter;
   (c) a multiple cloning site;
   (d) a nucleic acid; and
   (e) an SV40 poly A sequence;
wherein the 3' end of the plasmid construct does not comprise adenovirus map units 9-16 when compared to wild-type adenovirus.

2. The plasmid construct of claim 1, wherein said mammalian cells are human cells.

3. The plasmid construct of claim 1, further comprising a gene conferring antibiotic resistance to said mammalian cells.

4. The plasmid construct of claim 1, wherein said nucleic acid encodes wild type p53.

5. A liposome complex comprising (i) a liposome, (ii) a cell-targeting ligand, and (iii) the plasmid construct of claim 1.

6. A method of expressing a gene in a mammalian cell, comprising contacting the liposome complex of claim 5 with a mammalian cell under conditions suitable for transfection and gene expression.

* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic Primer

<400> SEQUENCE: 1
ggcccatgga ggtgcagctg gtgg                                              24

<210> SEQ ID NO 2
<211> LENGTH: 36
<212> TYPE: DNA
<213> ORGANISM: Artificial Sequence
<220> FEATURE:
<223> OTHER INFORMATION: Synthetic Primer

<400> SEQUENCE: 2
ccggaattcg cggccgcttt tatctccagc ttggtc                                 36

<210> SEQ ID NO 3
<211> LENGTH: 24
<212> TYPE: DNA
<213> ORGANISM: Artificial Sequence
<220> FEATURE:
<223> OTHER INFORMATION: Synthetic Primer

<400> SEQUENCE: 3
ggcccatgga ggtgcagctg gtgg                                              24

<210> SEQ ID NO 4
<211> LENGTH: 30
<212> TYPE: DNA
<213> ORGANISM: Artificial Sequence
<220> FEATURE:
<223> OTHER INFORMATION: Synthetic Primer

<400> SEQUENCE: 4
ggcgcggccg cgcattttat ctccagcttg                                        30

<210> SEQ ID NO 5
<211> LENGTH: 33
<212> TYPE: DNA
<213> ORGANISM: Artificial Sequence
<220> FEATURE:
<223> OTHER INFORMATION: Synthetic Primer

<400> SEQUENCE: 5
ggcgcggccg ctcagcattt tatctccagc ttg                                    33